(12) United States Patent
Everett et al.

(10) Patent No.: US 7,445,907 B2
(45) Date of Patent: Nov. 4, 2008

(54) METHODS FOR MASS SPECTROMETRY DETECTION AND QUANTIFICATION OF SPECIFIC TARGET PROTEINS IN COMPLEX BIOLOGICAL SAMPLES

(75) Inventors: Nicholas P. Everett, Meadow Vista, CA (US); James K. Petell, Brentwood, TN (US); Scott A. Young, Midland, MI (US)

(73) Assignee: ISTA S.p.A. (IT)

( * ) Notice: Subject to any disclaimer, the term of this patent is extended or adjusted under 35 U.S.C. 154(b) by 371 days.

(21) Appl. No.: 10/963,019

(22) Filed: Oct. 12, 2004
(Under 37 CFR 1.47)

(65) Prior Publication Data
US 2005/0153380 A1    Jul. 14, 2005

Related U.S. Application Data

(63) Continuation of application No. 10/475,206, filed as application No. PCT/US02/12014 on Apr. 17, 2002, now abandoned.

(60) Provisional application No. 60/284,273, filed on Apr. 17, 2001, provisional application No. 60/284,713, filed on Apr. 18, 2001.

(51) Int. Cl.
*C12Q 1/37* (2006.01)

(52) U.S. Cl. ............... 435/24; 250/287; 800/3; 800/4

(58) Field of Classification Search ............ None
See application file for complete search history.

(56) References Cited

U.S. PATENT DOCUMENTS

| | | | |
|---|---|---|---|
| 5,346,991 A | 9/1994 | Roy et al. | |
| 5,776,896 A * | 7/1998 | Lampe | 514/12 |
| 5,858,326 A | 1/1999 | Kisilevsky et al. | |
| 5,900,404 A * | 5/1999 | Gegg et al. | 514/12 |
| 5,977,324 A | 11/1999 | Prusiner et al. | |
| 5,977,442 A | 11/1999 | Klessig et al. | |
| 6,034,211 A | 3/2000 | Kelly | |
| 6,783,672 B2 * | 8/2004 | Tubbs et al. | 210/198.2 |

FOREIGN PATENT DOCUMENTS

| | | |
|---|---|---|
| WO | 99/12040 | 3/1999 |
| WO | 00/45168 | 8/2000 |

OTHER PUBLICATIONS

Aebersold et al., Ann. N.Y. Acad. Sci. 919:33-47 (2000).
Aguzzi et al., Nature Rev. 2:118-126 (2001).
Barnard et al., Luminescence 15:357-362 (2000).
Bolton et al., Science 218:1309-1311 (1982).
Boucherie et al., 17(11):1683-99 (1996).
Grassi et al., Arch Virol 16:197-205 (2000).
Gygi et al., Nat. Biotech. 17(10):994-999 (1999).
Mann et al., Anal. Chem. 66:4390-4399 (1994).
Münchbach et al., Anal. Chem. 72(17):4047-57 (2000).
Prusiner et al., Biochem. 21:6942-6950 (1982).
Prusiner, S., Science 216:136-144 (1982).
Prusiner, S., Science 252:1515-1522 (1991).
Schaller et al., Acta Neuropathol. 98:437-443 (1999).
Schmerr, et al., Electrophor. 19:409-414 (1998).
Scott et al., Proc. Natl. Acad. Sci. USA 96:15137-15142 (2000).
Yates et al., Anal. Chem. 67(8):1426-36 (1995).
Nilsson et al. New Separation Tools for Comprehensive Studies of Protein Expression by Mass Specvtrometry. Mass Spectrometry Reviews, 2000.
Gygi et al. Measuring gene expression by quantitative proteome analysis. Current Opinion in Biotechnology, 2000.
Alomirah et al., Applications of mass spectrometry to food proteins and peptides. Journal of Chromatography A, 2000.
Wilson. Mutiple hypenation of liquid chromatography with nuclear magnetic resonance spectroscopy, mass spectrometry and beyond. Journal of Chromatography A, 2001.
Favretto et al., Silicon Membrane Interface for the Direct Analysis of Kathon CG in Aqueous Solutions and Cosmetic Emulsions. Biological Mass Spectrometry, 1991, vol. 20, pp. 669-676.
Appel et al, Prion rods contain small amounts of two host sphingolipids as revealed by high preformance thin-layer chromatography and maldi mass spectrometry. Journal of Neurochemistry. 1999. vol. 73, Suppl., see abstract C, p. S159.
Nakanishi et al., Characterization of mutant proteins linked to neurodegenerative diseases by HPLC-ESIMS and the approaches for the researches of pathogentic etiologies of its related such as FAP and FALS. Nippon Iyo Masu Supekutoru Dakkai Koenshu. 1997, vol. 22, pp. 17-20, Abstract Only.
Baldwin, M.A. "Mass spectrometric analysis of prior proteins", Advances in Protein Chemistry, vol. 57 (prior proteins), pp. 29-54, 2001.
Desiderio, Zhu, "Quantitive analysis of methionine enkephalin and B-endorphin in the pitutitary by liquid secondary ion mass spectrometry and tandem mass spectrometry", Jouranl of Chromatography A, 794 (1998) 85-96.
Krekel F et al:"Substrate And Inhibitor-Induced Conformational Changes In The Structurally Related Enzymes UDP-N-Acetylglucosamine Enopyruvyl Trandferase (Mura) And 5-Enolpyruvylshikimate 3-Phosphate Synthase (EPSP)" Biochemistry, American Chemical Society. Easton, PA, US, vol. 38, No. 28, 1999, pp. 8864-8878.
geng M et al: "Signature-peptide approach to detecting proteins in complex mixtures"Journal Of Chromatography, Elsevier Science Publishers B.V. Amsterdam, NL, vol. 870, No. 1-2, Feb. 2000 (Feb. 2000), pp. 295-313.
Xue O et al: "Integrated Multichannel Microchip Electrospray Ionization Mass Spectrometry: Analysis Of Peptides From On-Chip Tryptic Digestion Of Melittin" Rapid Communications In Mass Spectrometry, Heyden, London, GB, vol. 11, 1997, pp. 1253-1256.
Vinale F et al.: "Development of a stable isotope dilution assay for an accurate quantification of protein-bound Nepsi Ion-(1-deoxy-D-fructos-1-yl ) -L-l ysine using a 13C- labeled internal standard" Journal Of Agricultural And Food Chemistry, American Chemical Society.Washington, US, vol. 47, No. 12, Nov. 18, 1999, (Nov. 18, 1999), pp. 5084-5092.

* cited by examiner

*Primary Examiner*—James S Ketter
(74) *Attorney, Agent, or Firm*—Lerner, David, Littenberg, Krumholz & Mentlik, LLP

(57) ABSTRACT

Mass spectrometry-based methods are described for the detection or quantification of targeted proteins in biological samples e.g., plants, animals, and microorganisms, parts (e.g., tissue or cells) thereof, and products derived from plants, animals or microorganisms.

25 Claims, 8 Drawing Sheets

FIG. 1

Predicted Differential Protease Cleavage Peptides of EPSPS

| Peptide Number* | Trypsin (KR) | Lys-C (K) | Arg-C (R) | Asp-N (D) | Glu-C (E) |
|---|---|---|---|---|---|
| 1 | 1328.5 | 1456.6 | 1328.5 | 2568.9 | 4477.0 |
| 2 | 146.2 | 1373.5 | 991.1 | 2996.3 | 902.1 |
| 3 | 862.9 | 3480.9 | 1109.2 | 2146.5 | 204.2 |
| 4 | 528.6 | 1232.5 | 1359.5 | 646.7 | 2089.5 |
| 5 | 598.7 | 5620.3 | 2375.7 | 1379.5 | 1784.0 |
| 6 | 1359.5 | 2080.5 | 287.4 | 1945.2 | 5144.9 |
| 7 | 1558.7 | 1639.8 | 3315.7 | 280.3 | 877.0 |
| 8 | 835.0 | 1860.2 | 3048.5 | 638.7 | 6098.1 |
| 9 | 287.4 | 2978.5 | 710.9 | 2912.4 | 1407.6 |
| 10 | 146.2 | 3005.4 | 1449.6 | 190.2 | 1345.5 |
| 11 | 3187.5 | 8224.5 | 697.9 | 5443.5 | 5557.5 |
| 12 | 2450.8 | 4332.0 | 1230.4 | 1991.2 | 634.7 |
| 13 | 615.8 | 1359.5 | 3279.9 | 204.2 | 1025.4 |
| 14 | 710.9 | 2316.5 | 2604.8 | 2068.4 | 2042.3 |
| 15 | 789.9 | 5950.9 | 388.5 | 386.4 | 1033.1 |
| 16 | 677.6 | 804.9 | 473.5 | 1742.0 | 1235.4 |
| 17 | 687.9 | 160.2 | 4375.1 | 2714.2 | 891.0 |
| 18 | 300.4 | | 2183.5 | 1382.5 | 147.1 |
| 19 | 948.1 | | 1115.2 | 303.3 | 643.8 |
| 20 | 930.1 | | 273.3 | 1757.0 | 2076.3 |
| 21 | 2367.8 | | 1388.5 | 788.9 | 204.2 |
| 22 | 628.6 | | 3250.7 | 3194.6 | 4292.0 |
| 23 | 1994.2 | | 732.8 | 1526.8 | 1808.0 |
| 24 | 388.5 | | 2559.9 | 236.2 | 1395.7 |
| 25 | 473.5 | | 2257.4 | 1414.5 | 704.8 |
| 26 | 203.2 | | 5251.1 | 1538.7 | |
| 27 | 4189.9 | | | 2315.7 | |
| 28 | 2183.5 | | | 133.1 | |
| 29 | 1115.2 | | | 1460.7 | |
| 30 | 273.3 | | | 1317.6 | |
| 31 | 534.6 | | | 504.5 | |
| 32 | 871.9 | | | | |
| 33 | 3250.7 | | | | |
| 34 | 245.3 | | | | |
| 35 | 505.5 | | | | |
| 36 | 872.0 | | | | |
| 37 | 1705.9 | | | | |
| 38 | 628.7 | | | | |
| 39 | 1646.8 | | | | |
| 40 | 4322.1 | | | | |
| 41 | 804.9 | | | | |
| 42 | 160.2 | | | | |

(amino acid cleaved)

single amino acid preferred size peptides

* from N-terminus

FIG. 3B

MSHGASSRPATARKSSGLSGTVRIPGDKSISHRSFMFGGL

ASGETRITGLLEGEDVINTGKAMQAMGARIRKEGDTWIID

GVGNGGLLAPEAPLDFGNAATGCRLTMGLVGVYDFDSTFI

GDASLTKRPMGRVLNPLREMGVQVKSEDGDRLPVTLRGPK

TPTPITYRVPMASAQVKSAVLLAGLNTPGITTVIEPIMTR

DHTEKMLQGFGANLTVETDADGVRTIRLEGRGKLTGQVID

VPGDPSSTAFPLVAALLVPGSDVTILNVLMNPTRTGLILT

LQEMGADIEVINPRLAGGEDVADLRVRSSTLKGVTVPEDR

APSMIDEYPILAVAAAFAEGATVMNGLEELRVKESDRLSA

VANGLKLNGVDCDEGETSLVVRGRPDGKGLGNASGAAVAT

HLDHRIAMSFLVMGLVSENPVTVDDATMIATSFPEFMDLM

AGLGAKIELSDTKAA

METHODS FOR MASS SPECTROMETRY DETECTION AND QUANTIFICATION OF SPECIFIC TARGET PROTEINS IN COMPLEX BIOLOGICAL SAMPLES

CROSS REFERENCE TO RELATED APPLICATIONS

This application a continuation of U.S. application Ser. No. 10/475,206 filed Oct. 17, 2003, which is a national phase entry under 35 U.S.C. § 371 of International Application PCT/US02/12014, filed Apr. 17, 2002, published in English, which claims benefit of U.S. Provisional Patent Application 60/284,273, filed Apr. 17, 2001, and U.S. Provisional Patent Application 60/284,713, filed Apr. 18, 2001. The disclosures of all of said applications are incorporated by reference herein.

TECHNICAL FIELD

The present invention relates generally to the use of mass spectrometry to detect, quantify, and characterize target proteins in complex biological samples.

BACKGROUND OF THE INVENTION

The development of sensitive, precise, high throughput methods for directly monitoring specific proteins is increasingly desirable for diagnostic applications in both agricultural and clinical fields. Recent advances in the use of mass spectrometry (MS) in conjunction with protein/DNA-sequence database search-algorithms allow for the identification of proteins with unprecedented speed (Mann and Wilm 1994, Yates et al 1995). Despite these advances, it remains difficult to obtain accurate quantitative information concerning the levels of the identified proteins and the levels of site-specific or other modifications to individual protein molecules.

The principal state-of-the-art approaches for quantitative analysis of individual proteins are enzyme-linked immunosorbent assays (ELISAs) and sandwich ELISAs (sELISAs). The crux of these methods is the binding of an antibody molecule that recognizes the protein or peptide of interest. The development of an ELISA for a target protein is a particularly laborious and lengthy task, which requires production of monospecific antibodies to one or more epitopes residing within the protein. An epitope is a single limited amino acid sequence that is recognized by the antibody. ELISA systems based on a monoclonal antibody recognize a single epitope on the target protein ELISA systems based on polyclonal antibodies tend to recognize more than one epitope. The ELISA reaction requires binding of an antibody that may or may not be covalently linked to a group that generates enzymatic-derived colorimetric product or elicits fluorescence. These end-products of an ELISA are used for quantitation.

ELISA methods have several shortcomings. These assays are indirect in the sense that they require multiple steps to produce a product that is quantifiable. In addition, the occurrence of false positives and negatives is not uncommon. Thus, they may have insufficient sensitivity for commercial diagnoses, particularly in cases where there is significant risk of legal liability in the event of an incorrect result. Further, ELISA-based assays are limited in that they can only detect analytes for which antibodies have been raised. This requires prior knowledge of sample composition coupled with time-consuming effort in order to prepare sufficient purified protein and raise a new antibody for each target protein or peptide species. All of these factors generally prevent ELISA-based assays from being applied to identify previously unknown species or variant derivatives of a known species within a sample. Thus, ELISA systems are unable to detect subtle changes to a target protein that may have a dramatic effect on its physical and biological properties. For example, the antibody might not recognize a specific form of the protein or peptide that has been altered by post-translation modification such as phosphorylation or glycosylation, or conformationally obscured, or modified by partial degradation. Identification of such modifications is vital because changes in the physical and biological properties of these proteins may play an important role in their enzymatic, clinical or other biological activities. Such changes can limit the reliability and utility of ELISA-based quantification methods.

In the absence of appropriate antibodies, quantification is usually achieved by autoradiography after metabolic radiolabeling, fluorography, or the use of protein stains. These procedures depend on complete separation of the proteins of interest by techniques such as chromatographic separation or high-resolution two-dimensional electrophoresis (Boucherie et al. 1996).

In the late 1980's two new mass spectrometries became available for the analysis of large biomolecules, namely, matrix-assisted laser desorption/ionization (MALDI) time-of-flight mass spectrometry (TOF MS) and electrospray ionization (ESI). Requiring only a minute sample, mass spectrometry provides extremely detailed information about the molecules being analyzed, including high mass accuracy, and is easily automated. Both of these instruments are capable of mass analyzing biomolecules in complex biological solutions. MALDI-TOF MS involves laser pulses focused on a small sample plate comprising analyte molecules embedded in a low molecular weight, UV-absorbing matrix that enhances sample ionization. The matrix facilitates intact desorption and ionization of the sample. The laser pulses transfer energy to the matrix causing an ionization of the analyte molecules, producing a gaseous plume of intact, charged analyte. The ions generated by the laser pulses are accelerated to a fixed kinetic energy by a strong electric field and then pass through an electric field-free region in a vacuum in which the ions travel (drift) with a velocity corresponding to their respective mass-to-charge ratios (m/z). The lighter ions travel through the vacuum region faster than the heavier ions thereby causing a separation. At the end of the electric field-free region, the ions collide with a detector that generates a signal as each set of ions of a particular mass-to-charge ratio strikes the detector. Travel time is proportional to the square root of the mass as defined by the following equation $t=(m/(2KE)z)^{1/2}$ where t=travel time, s=travel distance, m=mass, KE=kinetic energy, and z=number of charges on an ion. A calibration procedure using a reference standard of known mass can be used to establish an accurate relationship between flight time and the mass-to-charge ratio of the ion. Ions generated by MALDI exhibit a broad energy spread after acceleration in a stationary electric field. Forming ions in a field-free region, and then applying a high voltage pulse after a predetermined time delay (e.g. "delayed extraction™") to accelerate the ions can minimize this energy spread, which improves resolution and mass accuracy.

In a given assay, 50 to 100 mass spectra resulting from individual laser pulses are summed together to make a single composite mass spectrum with an improved signal-to-noise ratio. The entire process is completed in a matter of microseconds. In an automated apparatus, tens to hundreds of samples can be analyzed per minute. In addition to speed, MALDI-TOF technology has many advantages, which include: 1) mass range—where the mass range is limited by ionization ability, 2) complete mass spectrum can be obtained from a single ionization event (also referred to as multiplexing or parallel detection), 3) compatibility with buffers normally used in biological assays, 4) very high sensitivity; and 5) requires only femtomoles of sample. Thus, the performance of a mass spectrometer is measured by its sensitivity, mass resolution, and mass accuracy.

In order for mass spectrometry to be a useful tool for detecting and quantifying proteins, several basic requirements need to be met. First, targeted proteins to be detected and quantified must be concentrated (e.g., enriched and/or fractionated) in order to minimize the effects of salt ions and other molecular contaminants that reduce the intensity and quality of the mass spectrometric signal to a point where either the signal is undetectable or unreliable, or the mass accuracy and/or resolution is below the value necessary to detect the target protein. Second, mass accuracy and resolution significantly degrade as the mass of the analyte increases. Thus, the size of the target protein or peptide must be within the range of the mass spectrometry device where there is the necessary mass resolution and accuracy. Third, to be able to quantify accurately, one would preferably resolve the masses of the peptides by at least six Daltons to increase quality assurance and to prevent ambiguities. Fourth, the mass spectrometric methods for protein detection and quantification diagnostic screening must be efficient and cost effective in order to screen a large number of samples in as few steps as possible.

Mass spectrometry methods for the quantitation of proteins in complex mixtures have employed a system using protein reactive reagents comprised of three moieties that are linked covalently; an amino acid reactive group, an affinity group and an isotopically tagged linker group (Aebersold et al, 2000). This class of new chemical reagents is referred to as Isotope-Coded Affinity Tags (ICATs) (Gygi et al 1999). The reactive group embodied used sulfhydryl groups that react specifically with the amino acid cysteine. The presence of the affinity group facilitates the isolation of the specifically labeled proteins or peptides from a complex protein mixture. Selected affinity groups include strepavidin or avidin. Only those proteins containing these affinity groups may be isolated. The linker moiety may be isotopically labeled by a variety of isotopes that include $^3H$, $^{13}C$, $^{15}N$, $^{17}O$, $^{18}O$ and $^{34}S$. The use of differential isotopic ICATs provides a method for the quantitation of the relative concentration of peptides in different samples by mass spectrometry. The methods can be used to generate global protein expression profiles in cells and tissues exposed to a variety of conditions.

In an analogous method, the N-terminal amino acids of proteins from two states are differentially labeled using different isotopically tagged nicotinyl-N-hydroxysuccinimide reagents (Munchbach et al, 2000). Unlike the ICAT system, proteins are first separated by two-dimensional SDS polyacrylamide gel electrophoresis before the analysis is performed. The ratio of the isotope for each protein determined by mass spectrometry provides a relative concentration of each protein present in different physiological states.

It is believed that the limitations of mass spectrometry methods employing either ICATs or N-succinylation isotopic tagging are inherently associated with the requirement that the protein from one sample is quantified relative to another state or sample rather than being quantified in absolute amounts. In the case of the ICAT method, it is a requirement that the protein or peptide being quantified contains at least one amino acid that is modified by the reactive group. A related requirement is that the reactive amino acid site on the protein in the two or more states or samples must be equivalently accessible to the reactive group on the ICATs. Similar to antibody methods, if the site is altered or conformationally obscured then the quantitation of the protein will be compromised. An additional limitation in the use of N-succinylation of proteins is that it requires the laborious task of two-dimensional SDS polyacrylamide gel electrophoresis prior to analysis.

There remains a pressing need for easier, more reliable means to rapidly detect, quantify and characterize specific proteins from biologically complex samples.

SUMMARY OF THE INVENTION

The present invention provides a method for the detection and direct quantification of a targeted protein in complex biological samples utilizing mass spectrometry (MS).

A first aspect of the present invention is directed to a method of detecting a target protein in a complex biological sample (e.g., a product of biological origin), comprising:
(a) obtaining a biological sample;
(b) extracting proteins from the sample;
(c) concentrating the target protein from extracted proteins of (b);
(d) digesting concentrated proteins of (c) to produce peptide fragments of the proteins, wherein the fragments include at least one signature peptide specific to the target protein; and
(e) analyzying the peptide fragments via mass spectrometry, wherein detection of the at least one signature peptide is indicative of presence of target protein in the sample.

In some embodiments, the target protein is quantified by calculating the amount of the protein in the sample by comparing mass spectrometry signals generated from the signature peptide with mass spectrometry signals generated by its corresponding internal standard peptide. In preferred embodiments, the digesting produces peptide fragments containing at least two signature peptides and the analyzing comprises comparing mass spectrometry signals generated from at least one signature peptide with (mass spectrometry signals generated by an) its corresponding internal standard peptide. Thus, in embodiments where a plurality of signature peptides is generated, quantification of target protein in the sample entails comparing mass spectrometry signals generated from at least one signature peptide with those of (i.e., mass spectrometry signals generated by an) its corresponding internal standard peptide. The analyzing may also involve mass spectrometry signals generated from any of the other signature peptides without comparison to their corresponding internal standard peptides, simply for confirmation or to increase confidence level.

Another aspect of the present invention is directed to a method of quantifying a target protein which is an expression product of a transgene contained in a transgenic plant, tissue or cell, or for quantifying the target protein in a product derived from the transgenic plant, comprising:
(a) obtaining a sample from the transgenic plant or the product;
(b) extracting proteins from the sample;
(c) concentrating the target protein from extracted proteins of (b);
(d) digesting concentrated proteins of (c) (e.g., with a protease) to produce peptide fragments of the proteins, wherein the fragments include at least one signature peptide specific to the target protein;
(e) analyzying via mass spectrometry the peptide fragments and for at least one signature peptide, an internal standard peptide; and (f) calculating amount of the target protein in the sample by comparing mass spectrometry signals generated from the signature peptide with mass spectrometry signals generated by the internal standard peptide.

Yet another aspect of the present invention is directed to a method of quantifying a target protein which is an expression product of a transgene contained in a transgenic animal, tissue or cell, or for quantifying the target protein in a product derived from the transgenic animal, comprising:

(a) obtaining a sample from the transgenic animal or the product;

(b) extracting proteins from the sample;

(c) concentrating the target protein from extracted proteins of (b);

(d) digesting concentrated proteins of (c) (e.g., with a protease) to produce peptide fragments of the proteins, wherein the fragments include at least one signature peptide specific to the target protein;

(e) analyzying via mass spectrometry the peptide fragments and for at least one signature peptide, an internal standard peptide; and (f) calculating amount of the target protein in the sample by comparing mass spectrometry signals generated from the signature peptide with mass spectrometry signals generated by the internal standard peptide.

A further aspect of the present invention is directed to a method of quantifying a target protein which is an expression product of a transgene contained in a transgenic microorganism, or for quantifying the target protein in a product derived from the transgenic microorganism, comprising:

(a) obtaining a sample from the transgenic microorganism or the product;

(b) extracting proteins from the sample;

(c) concentrating the target protein from extracted proteins of (b);

(d) digesting concentrated proteins of (c) (e.g., with a protease) to produce peptide fragments of the proteins, wherein the fragments include at least one signature peptide specific to the target protein;

(e) analyzying via mass spectrometry the peptide fragments and for at least one signature peptide, an internal standard peptide, an internal standard; and (f) calculating amount of the target protein in the sample by comparing mass spectrometry signals generated from the signature peptide with mass spectrometry signals generated by the internal standard peptide. In preferred embodiments for each of these aspects, the digesting produces peptide fragments containing at least two signature peptides and the analyzing comprises comparing mass spectrometry signals generated from at least one signature peptide with mass spectrometry signals generated by an internal standard peptide for at least one of the signature peptides.

The methods of the present invention entail the digestion of the target protein so as to produce at least one signature peptide that is specific to the protein and perforce, not present in other proteins that may be present in the sample. They also entail the use of one or more calibrants or internal standard peptides having similar structure and molecular weight to the signature peptide, usually in a predetermined concentration. To quantify the targeted protein, the mass spectrometry signals generated from the signature peptide(s) and the internal standard peptide(s) are compared. The mass spectrometry analysis of the internal standard peptide or calibrant may be performed simultaneously with or separately from the biological sample.

The methods herein can be used for a variety of analyses in a wide variety of living organisms and in products derived therefrom. For instance, the methods may be applied to agricultural diagnostic analyses to detect the presence or absence of a targeted protein or set of targeted proteins in different types of tissue (e.g., seed, leaf, root, fruit) or in specific cell types or cell lines. The method is particularly useful in the detection of genetically modified organisms (GMOs) where a protein is being expressed, for example, for insect or herbicidal resistance, an enzyme or enzymes expressed to modify a metabolic pathway, and/or proteins are being expressed in plants for small and large-scale production. In addition, the method is suitable to diagnose phytopathogenic disease or contamination in plants, soils, liquids, solids, and other samples from environmental sources. The present invention can also monitor for targeted proteins in manufacturing food processes. Monitoring of microbial (e.g. bacterial, fungal, etc.) populations in bioremediation sites e.g., where a targeted protein or proteins are specific for the detection and/or quantification in plants, soils, liquids, solids, and other samples from the environmental sources, may also be accomplished using the present invention. the methods herein can be used for a variety of clinical and diagnostic analyses to detect the presence or absence, and levels of a protein or proteins in a biological fluid (e.g. urine, blood, serum, saliva, etc.) or in specific cell types or tissues in humans and animals. A further aspect of the present invention is the monitoring of infections (e.g. bacterial, fungal, viral, etc.) and their treatment in humans and animals.

The present ivention provides several advantages compared to current methods based on ELISA and mass spectrometry. One advantage of the present invention compared to ELISA is that it provides for a method for the direct quantitative measurement of the specific protein or peptide of interest in broad applications. Quantification of detected species can be completed simply using either internal or external calibrants that are modified synthetic peptides whose amino acid sequence is identical or nearly identical to the (signature fragments) of the protein(s) or peptide(s) to be quantified. The direct quantification is more efficient than current ELISA methods which require the lengthy and laborious production, preparation and maintenance of a uniform antibody for kits. In addition, it does not suffer from false positive and negatives as a result of indirect measurement. Unlike ELISA, the present methods can also be used to quantify proteins which may be post-translationally modified or processed. For example, one internal standard could be used to quantify the targeted protein, while a second internal standard for the same protein could be used to quantify a post-translational peptide or processed protein. The peptides or proteins from the different samples can be selectively quantified by mass spectrometry.

The present method for overcomes limitations associated with mass spectrometry sytems that quantify only relative concentrations by ICATs, N-succinylation or other mass spectrometry methods that involve chemical modification of the parent protein because it does not require the presence of specific amino acids that are accessible to reactive agents, or a second protein mixture for quantification. The present invention provides for multiple, simultaneous, independent analyses of the protein of interest, thereby significantly increasing the reliability of the diagnostic results obtained.

Beyond the foregoing, the invention described can be employed for the quantitative analysis of targeted proteins in complex biological mixtures as well as for simultaneous quantitative and qualititative analysis of multiple targeted proteins within a complex biological sample. Mass spectrometry is often the detection system of choice for structural characterization of analytes within complex biological mixtures due to its ability to specifically detect a wide range of analyte types. This makes MS ideal for the identification of unknown species during de novo research. Finally, MS analysis affords rapid and sensitive detection of a wide range of compounds at the low femtomole to high attomole range. The methods and reagents described herein can be employed in clinical and diagnostic assays for monitoring and quantifying targeted proteins from complex biological samples.

BRIEF DESCRIPTION OF THE DRAWINGS

FIG. 1 is a table that shows predicted differential protease cleavage peptides of 5-enolpyruvylshikimate-3-phosphate synthase (EPSPS).

FIG. 3B is an amino acid sequence (SEQ ID NO: 1) of EPSPS wherein underlined amino acids were detected by mass spectrometer.

FIGS. 6A and B are graphs of tryptic peptide mass fingerprint of EPSPS with spiked calibrants MP-1 and MP-2, wherein

DETAILED DESCRIPTION

Sample Types

Figure 2:
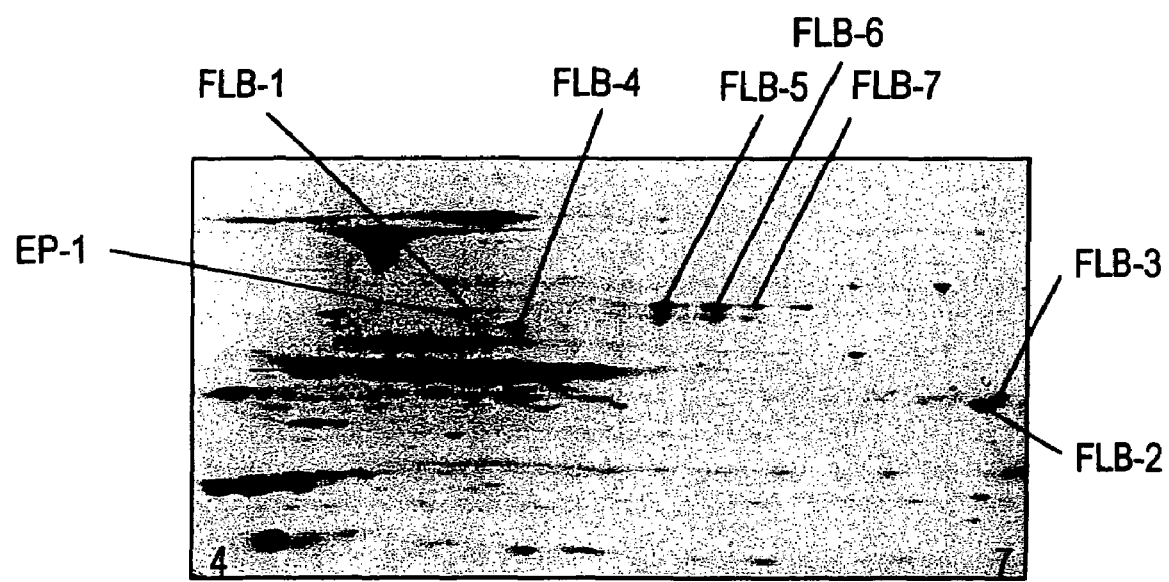
FIG. 2 is a photograph of a two dimensional gel electrophoresis of soybean seed proteins.

The present invention provides mass spectrometric processes for detecting and quantifying a targeted protein or proteins in a biological sample. For use in the invention, the biological sample should contain at least one protein.

As used herein, the term "biological sample" refers to any material directly or indirectly derived from any living source (e.g. plant, human, animal, microorganism such as fungi, bacteria, virus). Examples of appropriate biological samples for use in the invention include: tissue homogenates (e.g. biopsies), cell homogenates; cell fractions; biological fluids (e.g. urine, serum, cerebrospinal fluid, blood, saliva, amniotic fluid, mouth wash); and mixtures of biological molecules including proteins, DNA, and metabolites. The term also includes products of biological origin including pharmaceuticals, nutraceuticals, cosmetics, and blood coagulation factors, or the portion(s) thereof that are of biological origin e.g., obtained from a plant, animal or microorganism.

Any source of protein in a purified or non-purified form can be utilized as starting material, provided it contains or is suspected of containing the protein of interest. Thus, the target protein of interest may be obtained from any source, which can be present in a heterogeneous biological sample. The sample can come from a variety of sources. For example: 1) in agricultural testing the sample can be a plant, plant-pathogen, soil residue, fertilizer, liquid or other agricultural product; 2) in food testing the sample can be fresh food or processed food (for example infant formula, fresh produce, and packaged food); 3) in environmental testing the sample can be liquid, soil, sewage treatment, sludge, and any other sample in the environment which is required for analysis of a particular protein target; 4) in pharmaceutical and clinical testing the sample can be animal or human tissue, blood, urine, and infectious diseases.

As used herein "protein target" refers to a specific protein or set of proteins, which are being monitored, detected, and/or quantified in a biological sample. A protein target may be referred to as a protein marker, which is diagnostic for a given biological sample. The identity or function of the protein marker does not need to be known.

Protein Extraction

Protein can be isolated from a particular biological sample using any of a number of procedures, which are well known in the art, the particular isolation procedure chosen being appropriate for the particular biological sample. For example, soft plant tissues and animal tissues can be homogenized in the presence of appropriate cold buffers in a Waring Blender, polytron or sonicator; seeds may be macerated in a coffee grinder and further homogenized by mortar and pestle; bacteria and cell suspensions may be extracted by a French press, ultrasonication, or bead mill in the presence or absence of lysozymes; and red blood cells are easy to extract, after collection by centrifugation, and a rinsing step in isotonic NaCl, the cells are osmotically lysed with water or sonicated (Current Protocols in Protein Biochemistry, Cold Spring Harbor).

Concentration of Target Protein

Concentration of the target protein is desirable in order to obtain an appropriate quantity of a specific protein target on which to perform mass spectrometry. Concentration (e.g., enrichment) may be accomplished by any number of techniques and methods. Examples of appropriate means for concentration include the use of solid support resins (e.g. ion exchangers, affinity gel, and other resins that adsorb proteins). The resins may include beads (e.g. silica gel, controlled pore glass, Sephadex/Sepharose, cellulose, agarose,), that can be placed in columns (chromatography, capillary tubes), membranes or microtiter plates (nitrocellulose, polyvinylidenedifluoride, polyethylene, polypropylene), or on flat surfaces or chips or beads placed into pits in flat surfaces such as wafers (e.g. glass fiber filters, glass surfaces, metal surfaces (stainless steel, aluminum, silicon)). Alternatively, the beads may be added batchwise to protein solutions and then removed rapidly by centrifugation, filtration or magnetically (for magnetic beads). Such absorbents can capture or preferentailly absorb as much as 90% or more of the target protein. Other examples of concentration include gel electrophoresis, capillary electrophoresis, and pulsed field gel electrophoresis. The choice of a particular method will depend on a number of factors such as the amount of protein target present, the physical properties of the protein, the sensitivity required for the detection of the protein and the like. The method may also be designed such that the absorbent is specific to the target protein or non-target proteins.

In one embodiment of the present invention, a protein target is concentrated in a sample using polyacrylamide gels. The process involves homogenizing and extracting protein from a seed or leaf, adding the protein to either sodium dodecyl sulphate (SDS) polyacrylamide gel electrophoresis (PAGE) or to separate the proteins by isoelectric focusing followed by SDS-PAGE (referred to as 2-D gels). A protein band or protein spots can be excised from a gel, digested in situ by a chemical (e.g. CNBr) or proteolytic cleavage (e.g. trypsin), followed by elution of the digested peptide fragments. Techniques are also available for the mass spectrometry analysis of whole proteins from gels.

In a preferred embodiment of the present invention, a resin capable of adsorbing the target protein, such that the targeted protein is substantially (e.g., at least about 90%) dissociated from contaminating proteins, is used to enrich a protein target. A biological sample solution containing proteins is simultaneously enriched and filtered. The amount of sample that can be enriched using a given amount of resin can vary based upon the binding capacity of the resin. The simultaneous enriching and filtering procedure may be accomplished using a modified filtration technique. Filter techniques use devices such as filters and rely upon centrifugal or other driving force to wash and elute the sample through a structure such as a membrane. The size of the pores vary depending upon the protein target and biological sample. Any ultrafiltration device can be used to practice the present invention provided that the filter has a specific molecular weight cut-off. Such filters and ultrafiltration devices are commercially available from Millipore Corp., Bedford, Mass., or LifeScience Purification Technologies, Acton, Mass.

In accordance with various embodiments of the present invention, resin may be placed in a filtration device, for example, using the wells of a microtiter plate. The resin can be added to the microtiter plate in the form of beads. In this embodiment, the resin is added to microtiter wells, which contain a membrane at the bottom of the well through which the sample is allowed to be washed and eluted through the container into a receptacle. The biological sample solution is added to the microtiter plate containing the resin. The sample interacts with the resin and ions in the sample solution are exchanged for ions on the resin. Upon centrifugation or vacuum filtration, the protein targets absorbed to the resin may be washed or eluted off the resin and through the membrane filter. The enriched protein target is then collected from the receptacle.

Protease Digestion of Target Proteins

The enriched proteins are typically cleaved by a specific protease to generate peptide fragments. There are many different types of proteases one skilled in the art could use for cleaving proteins. For example: endoproteinase-Arg-C, endoproteinase-Aspn-N, endoproteinase-Glu-C (V8), endoproteinase-Lys-C, Factor Xa, papain, pepsin, thermolysin, and trypsin, are examples of endopeptidases. It is also possible to use a chemical compound, which may cleave at specific amino acids (e.g. CNBr, cleaves at methionines). Proteases and chemicals generate different peptide fragment lengths and thus different peptide masses. As illustrated in FIG. 1, for example, the glyphosate resistant gene, 5-enolpyruvylshikimate-3-phosphate (EPSPS), is differentially cleaved into numerous peptides with distinct mass sizes. Two or more proteases may be used to enhance the production of desired peptides either sequentially or concurrently. The peptides are preferably in the range from about 900 to 2500 Da but are not limited to these molecular sizes.

Selection of Signature Diagnostic Peptides

Sequence-Dependent Proteins

The targeted protein can be digested e.g., cleaved by a specific protease, to generate a family of peptide fragments that can be analyzed by mass spectrometry to generate a peptide mass fingerprint. As used herein the term "signature peptide masses" refers to the peptide masses generated from a particular protein target or targets, which can used to identify the protein target. Those peptide masses from a given peptide mass fingerprint which ionize easily and have a high mass resolution and accuracy, are considered to be members of a set of signature diagnostic peptide masses for a given target. The pattern is is unique and thus distinct for each protein. A "sequence-dependent protein" is a protein for which the amino acid sequence is already known (e.g., from gene sequencing). One skilled in the art will recognize that peptide mass fingerprints generated from a protein target can be easily compared with predicted peptide mass fingerprints generated in silico and predicted masses of a target protein. Thus, the location of where these peptide masses reside in a given target protein can be determined (e.g. a peptide fragment may reside near the N-terminus or C-terminus of a protein).

The observed peptide masses of a targeted protein can be compared with in silico-predicted masses of a targeted protein for which the amino acid sequence is known. Those peptide masses from a given peptide mass fingerprint, which ionize easily and have high mass resolution and accuracy are considered to be members of a signature diagnostic peptide masses for a given target. For a sequence-dependent protein that is not available in purified form for peptide mass fingerprinting, signature diagnostic peptides can be selected by chemically synthesizing peptides corresponding to predicted peptide fragments from a particular target protein/proteinase combination and then determining their physico-chemical properties and behavior in the mass spectrometer. During peptide synthesis, a portion of the peptide can be chemically modified (e.g. by acetylation) to provide internal calibrants or internal self-calibrants for inclusion in the set of peptide mass fingerprints to be analyzed by mass spectrometry. The inclusion of such chemically modified synthetic peptides facilitates improved mass accuracy and quantitation.

Sequence-Independent Proteins

The present invention also includes the identification of signature diagnostic peptide masses of a sequence-independent protein target. A "sequence-independent" protein is a protein where the amino acid sequence is not known initially, however the protein could be a known marker for a specific physiological or genetic state. Sequence-independent proteins can be purified by standard proteomics techniques, such as two-dimensional gel electrophoresis, and cleaved by a specific protease to generate a peptide mass fingerprint determined by mass spectrometry. Peptides that are not well represented in the peptide mass fingerprint would be excluded from the set of potential signature diagnostic peptides. One skilled in the art will recognize that the order of these peptides in the progenitor protein may not be known. Amino acid sequencing may be accomplished by several means, a chemical method Edman degradation or by post-source decay (PSD) analysis on a mass spectrometry instrument. PSD analysis is an acquisition method tailored to the analysis of fragment ions. PSD mode allows for better analysis of ion fragments in the flight tube by optimizing the mirror ratio and precursor ion selector. The choice of measurement method depends in part on the purity of the protein and the quantity of the protein to be analyzed.

Detection and Quantitation of Peptides by Mass Spectrometry

Once a set of signature diagnostic peptide masses have been identified either from a sequence-dependent or sequence-independent protein target, it is possible to detect or determine the absolute amount of the targeted protein in a complex mixture by synthesizing the internal standards in the mass spectrometer. For quantification, a known amount of internal standards, at least one such peptide and in preferred embodiments, two for each specific protein in the mixture to be detected or quantified, are added to the sample to be analyzed. In particular, the internal standard peptides are identical to peptides which have originated from the targeted protein, except that they are modified to distinguish them from the mass of the equivalent signature peptide to be quantified. Qualitative analysis does not require presence of the internal standard peptide.

In an embodiment of the present invention the use of internal standard-peptides are used not only to detect but also determine the absolute amount of the target protein or proteins in a complex mixture. These internal standard peptides are of particular use to monitor and quantify the target protein. In this application, the internal standard peptide is chemically identical to a peptide fragment determined from a signature diagnostic peptide mass fingerprint, except that the peptide has been modified in such a way that there is a distinct mass difference compared to the parent mass that allows it to be independently detected by MS techniques. One skilled in the art can synthesize the amino acid sequence and modify a specific amino acid to distinguish the peptide from the parent peptide. For example, peptides can be modified by acetylation, amidation, anilide, phosphorylation, or by substituting one or more atoms of one or more amino acids with a stable isotope to generate one or more substantially chemically identical, but isotopically distinguishable internal standard peptides. For example, any hydrogen, carbon, nitrogen, oxygen, or sulfur atoms may be replaced with isotopically stable isotopes: $^{2}H$, $^{13}C$, $^{15}N$, $^{17}O$, or $^{34}S$. The internal standard peptides can be used in the method described herein to quantify one or several protein targets in a biological sample.

In one aspect, the invention provides a mass spectrometric method for detection and quantification of one or more proteins from a complex biological solution, which employs a resin in which the resin can separate or absorb targeted proteins based upon the properties of the targeted protein. Such that the targeted protein will either absorb to the resin or contaminating proteins will absorb to the resin. It may be necessary to wash the resin to remove contaminating proteins and thus reducing the complexity of the biological solution. Following a wash step the targeted protein or proteins may be eluted with specific buffers to dissociate the protein. After the proteins have been eluted, the proteins are digested e.g., with a specific protease to generate peptide masses, which can be analyzed by mass spectrometry techniques. Signature diagnostic peptide masses will provide the information as to whether or not the targeted protein or proteins have been detected in the complex biological solution. The proteolytic step may not be necessary, if the targeted proteins can be detected directly by the mass spectrometer with sufficient accuracy to avoid confusion with other non-target proteins.

Quantification of targeted proteins in one or more different samples containing protein mixtures (e.g. biological fluids, cell or tissue lysates etc.) can be determined using identical peptides based upon in silico proteolytic digests of targeted proteins, which have been modified as to change the mass. The amounts of a given targeted protein in each sample is determined by comparing the abundance of the modified peptides from any modified peptide originating from that protein. The method can be used to quantify amounts of known proteins in different samples. More specifically, the method can be applied to screen for and identify proteins, which exhibit differential expression in cells, tissue or biological fluids. It is thus possible to determine the absolute amounts of specific proteins in a complex mixture. In this case, a known amount of internal standard, at least one for each specific protein in the mixture to be quantified is added to the sample to be analyzed. The internal standard is identical to the peptide from which it originated except that it is modified to distinguish it from the signature peptide mass to be quantified. The internal standard can be provided in the sample to be analyzed in other ways. For example, a specific protein or set of proteins can be monitored by multiple internal peptides to detect and quantify several targeted proteins simultaneously.

Accurate quantification of the target protein is achieved through the use of synthetically modified peptides that have amino acid identity, or near identity, to signature diagnostic peptides and have been predetermined for molecular weight and mass. The typical quantification analysis is based on two or more signature diagnostic peptides that are measured to reduce statistical variation, provide internal checks for experimental errors, and provide for detection of post-translation modifications. The method of this invention can be used for qualitative and quantitative analysis of single or multiple targeted proteins in complex biological samples for a variety of applications that include agricultural, food monitoring, pharmaceutical, clinical, production monitoring, quality assurance and quality control, and the analysis of environmental samples.

To facilitate mass spectrometric analysis, peptides and proteins generated from either "in-gel" proteolysis or from biological solutions may be concentrated, desalted, and detergents removed from peptide or protein samples by using a solid support. Examples of appropriate solid supports include $C_{18}$ and $C_4$ reversed-phase media, ZipTip (Millipore). Immobilization of peptides or proteins can be accomplished, for example, by passing peptides and proteins through the reversed-phase media the peptides and proteins will be adsorbed to the media. The solid support-bound peptides or proteins can be washed and then eluted, which improves overall detection by mass spectrometry.

Preferred mass spectrometer formats for use in the invention are matrix assisted laser desorption ionization (MALDI) and electrospray ionization (ESI). For ESI, the samples, dissolved in water or in a volatile buffer, are injected either continuously or discontinuously into an atmospheric pressure ionization interface (API) and then mass analyzed by a quadrupole. The generation of multiple-charged ion peaks, which can be obtained using ESI mass spectrometry, can increase the accuracy of the mass determination. Even more detailed information on the specific structure can be obtained using an MS/MS quadrupole configuration. For a more detailed discussion and comparison of various mass spectrometry technologies, see Siuzdak, *Mass Spectrometry for Biotechnology*, Academic Press (1995).

In MALDI mass spectrometry, various mass analyzers can be used, e.g., magnetic sector/magnetic deflection instruments in single or triple quadrupole mode (MS/MS), Fourier transform and time-of-flight (TOF) configurations as is known in the art of mass spectrometry. For the desorption/ionization process, numerous matrix/laser combinations can be used. Ion trap and reflectron configurations can also be employed.

Mass spectrometers are typically calibrated using analytes of known mass. A mass spectrometer can then analyze an analyte of unknown mass with an associated mass accuracy and precision. However, the calibration, and associated mass accuracy and precision, for a given mass spectrometry system can be significantly improved if analytes of known mass (e.g., molecular weight) are contained within the sample containing the analyte(s) of unknown mass(es). The inclusion of these known mass analytes within the sample is referred to as use of internal calibrants. The preferred practice is to add known quantities of the calibrant. For MALDI-TOF MS, generally only two calibrant molecules are needed for complete calibration, although sometimes three or more calibrants are used. All of the embodiment of the invention described herein can be performed with the use of internal calibrants to provide improved mass accuracy.

One skilled in the art will readily recognize that the method described in this invention has many advantages. It can be readily modified for automated detection and quantification of target proteins. In one embodiment of the present invention is a machine for processing the sample, enriching the protein target, cleaving the protein target, and transferring the peptides to mass spectrometry for detection and quantification of the peptide masses, and a computer means for recording and outputting the results of the MS spectra. Another embodiment is a kit for the detection of a specific target protein in specific sample types, which provides the user with reagents that have been customized for a particular target protein. Thus, in preferred embodiments, the kit contains extraction buffer(s), enrichment resin(s), protease(s), synthetic diagnostic peptide(s) and internal standard peptide(s), and precise instructions on their use.

The methods, instruments and procedures described herein can be used for a variety of purposes. Because of the sensitivity and specificity of the analysis one skilled in the art will readily recognize uses for this methodology. What follows is a representative list of uses in specific areas where a current need exists for a quick and reliable analysis.

The methodology of the present invention is useful in the areas of agriculture. One can monitor genetically modified organisms (GMO's) in all agricultural crops where a protein is being transgenically expressed. Detecting or quantifying the target proteins that are specific to a genetically modified organism is important for diagnosing or monitoring levels of such proteins and determining whether a product or sample is "GMO-free". Examples of genetically modified organisms, which may be detected and quantified by the disclosed processes include: glyphosate tolerant (e.g. corn, beet, rapeseed, soybean, cotton), phosphinothricin tolerant (e.g. rapeseed, beet, corn, soybean, rice), bromoxynil tolerant (e.g. cotton), lepidopteran resistant (e.g. corn, tomato, cotton), Colorado potato beetle resistant (e.g. potato), PLRV resistant (e.g. potato), PVY resistant (e.g. potato), male sterile (e.g. corn), corn root worm resistant (e.g. corn), CPB resistant (e.g. potato), modified oil profile (e.g. rapeseed, soybean), European core borer resistant (e.g. corn), sulfonylurea tolerant (e.g. cotton), and potato beetle resistant (e.g. potato).

This procedure is very useful in the area of monitoring plant pathogens. One can monitor plants that have been infected by any number of different pathogens. Examples of plant pathogens which could be monitored include: viruses (e.g. African cassaya mosaic virus, alfalfa mosaic virus, apple chlorotic leaf spot virus, apple mosaic virus, banana bunchy top virus, banana streak virus, barley stripe mosaic virus, barley yellow dwarf virus, cauliflower mosaic virus, cucumber mosaic virus, maize streak virus, papaya mosaic virus, potato virus Y, soybean mosaic virus, tobacco mosaic virus, wheat streak mosaic virus); viroids (e.g. chrysanthemum stunt viroid, potato spindle tuber viroid); fungi (e.g. *phytophthora, verticillium dahliae*); and bacteria (e.g. *clavibacter michiganensis* subs. *Michiganensis, erwinia amylovora, erwinia carotovora, erwinia chrysanthemi, erwinia stewartii, pseudomonas* and *xanthomonas*).

This procedure is very useful in the area of monitoring food contamination. Food producers currently test their products for specific contamination (e.g. microorganisms, genetically modified organisms). The present invention will facilitate this testing.

Another application of this method is in the manufacturing process. A number of manufacturing processes for fermentation processes, food manufacturing, chemical manufacturing, and drugs rely on the detection and quantification of protein markers. In either case the method of the present invention can be used. It can also be used for quality control in monitoring protein levels in laboratory tests.

The following examples are offered by way of example, and are not intended to limit the scope of the invention in any manner.

EXAMPLE 1

Predicted Proteolytic Cleaveage of 5-enolpyruvylshikimate-3-phosphate synthase Present in Genetically Modified Plants For those proteins that correspond to genes that have been cloned and sequenced, such as for 5-enolpyruvylshikimate-3-phosphate synthase (EPSPS), its amino acid sequence can be readily deduced from the DNA sequence. The deduced amino acid sequence of EPSPS was subjected to theoretical or in silico protease digestion using 5 distinct proteases. Three of the proteases cleave at basic amino acid sites (trypsin, Arg-C, Lys-C) and the two other proteases at acidic sites (Asp-N and Glu-C). Arg-C and Lys-C cleave at the carboxy-terminus of arginine and lysine residues, respectively. Trypsin cleaves at two amino acid sites, lysine and arginine residues. Asp-N cleaves at amino-terminus of aspartic residues while Glu-C cleaves at the carboxy-terminus of glutamic residues.

In FIG. 1, the peptides cleaved by the five proteases are listed from the amino-terminus to the carboxy-terminus. The preferred peptides masses range from 900 to 2500 daltons in molecular size. As illustrated by trypsin cleavage (two sites), in the event that single amino cleavage does provide a sufficient number of peptides, a second protease may be used to increase the number of preferred peptide molecular sizes. The additional number of peptides generated by two-site cleavage provided an increased and better distribution of peptides throughout the entire protein.

EXAMPLE 2

Enrichment of 5-enolpyruvylshikimate-3-phosphate synthase EPSPS from Soybean Seeds Enrichment of 5-enolpyruvylshikimate-3-phosphate synthase from transgenic soybean seeds.

The initial step for the detection and quantitation of a GM protein in plants is to obtain a protease digest profile of peptides for the protein of interest. The protein may be available in large amounts from a recombinant source such as bacteria or insect (baculovirus expressed) cells. Alternatively, transgenic plants expressing sufficient levels of the protein may provide the material required for peptide profiling. For EPSPS, the latter source was used as the source for peptide profiling.

The plant material was subjected to a series of enrichment protocols for the identification of EPSPS and was preliminarily identified when comparing colloidal stained 2-D gel patterns of proteins isolated from non-transformed and transgenic soybean seeds expressing EPSPS.

Ten seeds were ground in a pre-chilled coffee grinder to a fine powder. The powder was transferred to a mortar and homogenized with the addition of 6 mL of ice cold extraction buffer containing 100 mM Tris HCl, pH 7.8, 5 mM magnesium chloride, 100 mM sodium borate, 0.2% sodium ascorbate, and 0.05% v/v Tween 80. The slurry was transferred to a 2 mL Kontes glass tissue grinder for further homogenization. The homogenate was transferred to a 1.5 mL microfuge tube, sonicated for 5 min., and chilled on ice for 10 minutes. This procedure was repeated twice. Insoluble cellular debris was removed by centrifuging the homogenate for 10 min. at 14,000 g. The supernatant was decanted into a clean 1.5 mL microfuge tube. The Bio-Rad Protein Assay kit using a bovine gamma globulin standard was used to determine the protein concentration of the supernatant.

The resulting soluble proteins were next characterized by high-resolution two dimensional gel electrophoresis. Proteins (420 µg) were solubilized for isoelectric focusing (IEF) analysis in rehydration sample buffer consisting of 5 M urea, 2 M thiourea, 2% (w/v) CHAPS, 2% (w/v) SB 3-10, 40 mM Tris, 2 mM tributyl phosphine (added to rehydration solution just before use), and 0.2% Bio-Lyte 3/10. Protein/rehydration solution was rehydrated into 11 cm IPG ReadyStrip pH 3-10 under passive conditions: 0 volts, 20° C., 16 hrs.

One-dimensional isoelectric focusing was carried out on a Protean IEF cell (Bio-Rad) for 35,000 volt-hours using IPG ReadyStrips (Bio-Rad). Following first dimension electrophoresis, gels were equilibrated for 20 minutes in a buffer containing 20% glycerol, 0.375 M Tris, 6 M urea, 2% SDS, and 5 M tributyl phosphine. IPG ReadyStrips were placed on top of a Criterion™ precast 1 mm 4-20% gradient Tris-HCl-SDS gel (Bio-Rad) and 0.5% warm Agarose containing 0.01% bromophenol blued was added to the remaining well. Electrophoresis was carried out on a Criterion mini electrophoresis cell (Bio-RAD) at room temperature. The electrophoresis running buffer was prepared from a 10X Tris-glycine-SDS solution (Bio-RAD). Following assembly of the gel system and addition of the running buffer, the electrophoresis was carried out at an initial current of 2 mA, 3500 volts, 45 watts, for 1.5 hrs. The current was ramped up to 5 mA for 30 minutes followed by 10 mA for 2-3 hrs. Typical run times were between 4-5 hrs. Following electrophoresis, gels were stained in a buffer consisting of 17% ammonium sulfate, 30% methanol, 3% phosphoric acid, and 0.1% coomassie brillant blue G250, for at least 12 hrs. Gels were rinsed with water and stored in 2% acetic acid until further processing.

Colloidal Coomassie-stained gel images were captured using an EPSON 1200 photo imager. Digital filtering algorithms were used to remove non-uniform background without removing critical image data. Internal standards 2-D gel standards were used initially to precisely determine the molecular weight and isoelectric point of targeted proteins of interest.

5-enolpyruvylshikimate-3-phosphate synthase preliminary identification by 2-D gel differential display.

As described previously, 2-D gel electrophoresis displays were obtained by separating and resolving proteins isolated from either non-transformed or transgenic soybean seeds expressing EPSPS. FIG. 1 shows a typical protein pattern by transgenic soybean seeds expressing EPSPS. Approximately 50 proteins were resolved per gel in this specific quadrant. Most of the proteins observed were always present in different pools of 10 seeds analyzed.

FIG. 2 illustrates a 2-D gel display of EPSPS expressed transgenic soybean seed proteins. EPSPS is the only protein which was differentially present in the transgenic material, but not in the non-transformed soybean seed differential display. The remaining proteins were present in both 2-D gels. The one protein having a molecular weight of approximately 48 kDa and a pI of 5.2 is unique to the transgenic soybean seed sample (labeled in FIG. 2). The protein labeled EP-1 was reproducibly detected in all samples analyzed which had been previously identified as being transgenic for EPSPS. Table 1 identifies proteins, designated either as FLB-1 through FLB-7 or EP-1, by their approximate molecular weight and isoelectric point. Both the molecular weight and isoelectric point values listed in Table 1 are approximate and accurate to within 3,000 Daltons for molecular weight and to within 0.2 pI units for isoelectric point.

TABLE 1

Related and un-related proteins from non-transformed and transgenic soybean seed lines expressing EPSPS.

| Protein ID | MW (kDa) | pI | Non-transgenic | Transgenic |
|---|---|---|---|---|
| FLB-1 | 52 | 5.1 | + | + |
| FLB-2 | 40 | 6.8 | + | + |
| FLB-3 | 42 | 6.9 | + | + |
| FLB-4 | 48 | 5.5 | + | + |
| FLB-5 | 53 | 5.7 | + | + |
| FLB-6 | 53 | 5.9 | + | + |
| FLB-7 | 53 | 6.1 | + | + |
| EP-1 | 48 | 5.2 | − | + |

Proteins FLB-1 through FLB-7 were reproducibly detected in all soybean seed lines and pools of seeds tested, these proteins had a distinct pattern and were further characterized to rapidly monitor the presence or absence of EP-1 relative to both the molecular weight and isoelectric point. EP-1 was detected only in those lines or pools of seeds, which were identified as having the EPSPS gene.

EXAMPLE 3

Identification of Diagnostic Marker Peptides for 5-enol-pyruvylshikimate-3-phosphate synthase and beta-conglycin in Soybean Seeds Identification of EP-1 and FLB-1 FLB-7 diagnostic protein markers.

The eight protein spots detectable on a 2-D gel corresponding to EP-1 and FLB-1 through FLB-7 were excised, proteolytically cleaved, analyzed and identified as described below.

Identical protein spots from 1-3 gels were excised manually and pooled. The gel pieces were macerated and destained with 25 mM ammonium bicarbonate/50% acetonitrile in a 1.5 mL microfuge tube with vigorous shaking for 30 minutes. The blue-tinted destaining solution was removed and discarded with a fine-tip pipette. The destaining step was repeated until the stain was removed from the gel pieces. The gel pieces were dried under vacuum for 10 to 15 minutes. Proteins were digested overnight at 37° C. in a total volume of 25 µL of sequence-grade, modified trypsin (Roche Diagnostics) at a final protein of 25 ng/µL in 25 mM ammonium bicarbonate. Peptides were eluted with 50% acetonitrile and 0.5% trifluoroacetic acid. All peptide samples were concentrated, desalted, and detergents removed by using either $C_4$ or $C_{18}$ reversed-phase ZipTip™ pipette tips as described by the manufacturer (Millipore).

The resulting tryptic peptides were analyzed directly by mass spectrometry. All mass spectrometry experiments were carried out on a PerSeptive Biosystems (Framingham, Mass.) Voyager DE-STR equipped with a $N_2$ laser (337 nm, 3-nsec pulse width, 20-Hz repetition rate). The mass spectra were acquired in the reflectron mode with delayed extraction. Internal mass calibration was performed with low-mass peptide standards, and mass-measurement accuracy was typically ±0.1 Da. All peptide samples were diluted in α-cyano-4-hydroxycinnamic acid, which had been prepared by dissolving 10 mg in 1 mL of aqueous 50% acetonitrile containing 0.1% trifluoroacetic acid. The measured tryptic peptide masses were used as inputs to search the NCBInr5.13.99 database. All searches were carried out using the Protein Prospector software developed at UCSF. No restrictions were placed on the species of origin of the protein. The allowed protein molecular mass range was 1,000 to 150,000 Da. Isoelectric points were allowed to range from 3.0 to 10.0, and oxidation of Met was included as a side reaction. Up to one missed tryptic cleavage was considered, and a mass accuracy of ±0.5 Da was used for all tryptic-mass searches. The number of tryptic peptides required for identification varied as a function of the quality of the MALDI mass spectra.

Diagnostic protein markers for EP-1 were identified.

Figure 3A:
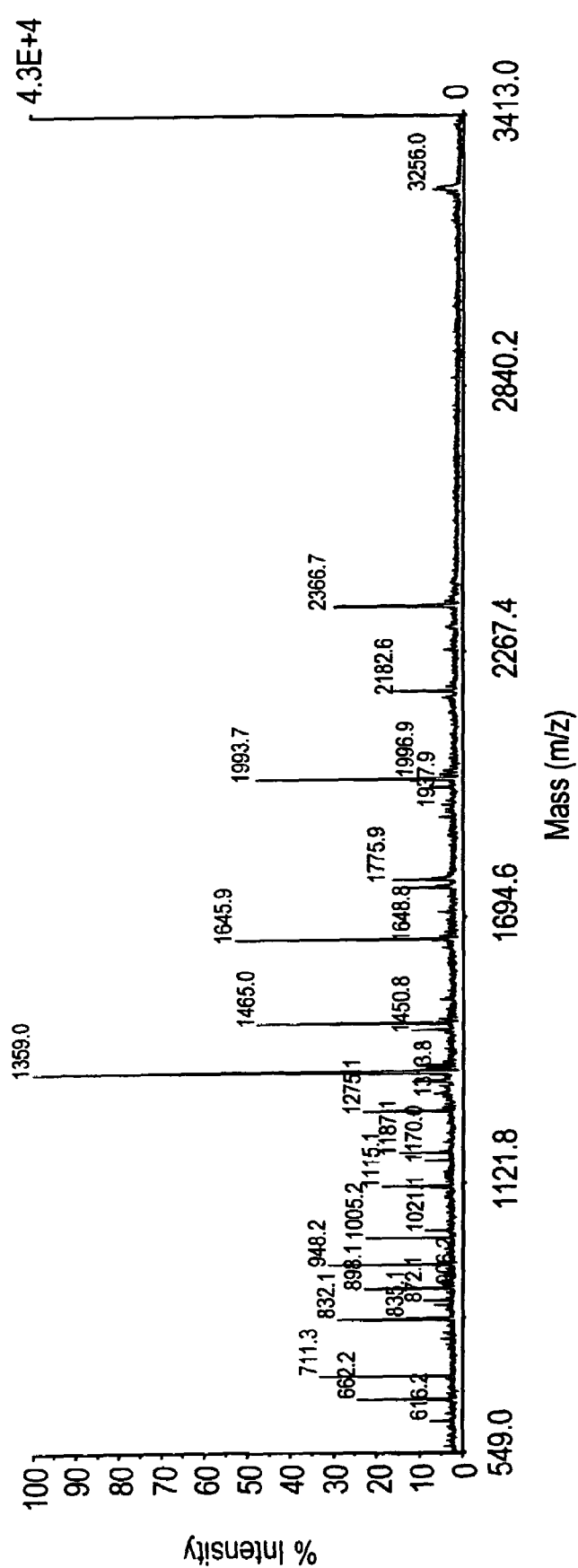
FIG. 3A is a graph showing a tryptic peptide mass fingerprint of EPSPS excised from SDS-PAGE.

Using the methodology described above, EP-1 (MW 48 kDa, pI 5.2) was isolated from three 2-D gels of transgenic soybean seeds encoding the EPSPS gene, digested with trypsin, and the peptides were extracted. The resulting peptide mixture was analyzed directly by MALDI-MS. Correlation of the determined masses with the EPSPS sequence is shown in Table 2. Eight diagnostic tryptic peptide masses were identified, which covers 30.4% of the EPSPS sequence (FIGS. 3A and 3B).

Diagnostic protein markers FLB-1 FLB-7 were identified.

Peptide mass fingerprints were generated for seven distinct proteins, which were used as reference markers to identify the presence or absence of EP-1 (Table 3). The tryptic map of each protein spot contained approximately 25 resolved peaks. Mass analysis was performed on each peptide mass fingerprint to identify each protein. Searching the NCBR database identified two of the seven proteins. FLB-1 with an apparent molecular weight of 52 kDa suggests identification of the protein by 16 matches of 22 tryptic peptide masses (Table 4). These matches suggest the identification of a soybean beta-conglycinin, alpha chain precursor.

TABLE 2

Peptide masses obtained by MALDI-MS of the 48 kDa, pI 5.2 EP-1 protein spot digested with trypsin.

| Observed M + H | Predicted M | Sequence | Residues of SEQ ID NO: 1 |
|---|---|---|---|
| 711.2 | 710.9 | VLNPLR | 133-138 |
| 948.1 | 948.1 | TPTPITYR | 161-168 |
| 1358.9 | 1359.5 | SFMFGGLASGETR | 34-46 |
| 1645.9 | 1646.8 | GLGNASGAAVATHLDHR | 389-405 |
| 1993.7 | 1994.2 | MLQGFGANLTVETDADGVR | 206-224 |
| 2182.6 | 2183.5 | TGLILTLQEMGADIEVINPR | 275-294 |
| 2366.6 | 2367.8 | SAVLLAGLNTPGITTVIEPIMTR | 178-200 |
| 3250.2 | 3250.7 | APSMIDEYPILAVAAAFAEGATVMNGLEELR | 321-351 |

*underlining reflects sequences confirmed by MALDI-PSD.

Sequence tags were obtained from EP-1 to definitively identify the protein by mass spectrometry. Post source decay (PSD) fragment ion spectra were acquired for two peptides (1358.9 and 1646.8 m/z) after isolation of the appropriate precursor ion by using timed ion selection. Fragment ions were refocused onto the final detector by stepping the voltage applied to the reflector in the following ratios: 1.0, 0.913, 0.842, 0.756, 0.605, 0.412, 0.274, 0.198, and 0.121 (fragment segments). The individual segments were stitched together by using software provided by PerSeptive Biosystems. All precursor ion segments were acquired at low laser power (variable attenuator=1,450) for <256 laser pulses to avoid saturating the detector. The laser power was increased for all of the remaining segments of the PSD acquisitions. Typically, 256 laser pulses were acquired for each fragment-ion segment. The PSD data were acquired at a digitization rate of 20 MHz. Mass calibration was performed with peptide standards. Metastable decompositions were measured in all PSD mass spectrometry experiments. The PSD analysis verified the amino acid sequence of both 1358.9 and 1646.8 m/z peptide masses.

TABLE 3

Peptide masses obtained by MALDI-MS of seven proteins excised from 2-D gels and digested with trypsin.

| FLB-1 52 | FLB-2 48 | FLB-3 52 | FLB-4 48 | FLB-5 42 | FLB-6 42 | FLB-7 38 |
|---|---|---|---|---|---|---|
| 564.1 | 568.0 | 653.1 | 564.2 | 568.0 | 545.3 | 545.3 |
| 621.1 | 634.1 | 659.2 | 621.3 | 745.3 | 564.2 | 564.3 |
| 637.0 | 662.1 | 745.2 | 659.2 | 797.2 | 568.1 | 659.3 |

TABLE 3-continued

Peptide masses obtained by MALDI-MS of seven proteins excised from 2-D gels and digested with trypsin.

| FLB-1 52 | FLB-2 48 | FLB-3 52 | FLB-4 48 | FLB-5 42 | FLB-6 42 | FLB-7 38 |
|---|---|---|---|---|---|---|
| 784.1 | 722.9 | 797.1 | 712.2 | 897.2 | 627.3 | 876.9 |
| 859.0 | 804.0 | 890.0 | 720.1 | 973.2 | 659.3 | 956.3 |
| 955.0 | 832.0 | 892.0 | 807.2 | 1036.2 | 745.3 | 1064.4 |
| 1051.0 | 890.0 | 948.1 | 859.3 | 1065.3 | 775.3 | 1112.3 |
| 1079.0 | 943.8 | 973.1 | 915.2 | 1090.1 | 797.2 | 1179.3 |
| 1169.9 | 1020.1 | 989.0 | 955.2 | 1142.2 | 897.2 | 1201.2 |
| 1187.8 | 1180.0 | 1036.1 | 1036.2 | 1158.2 | 956.3 | 1235.2 |
| 1244.0 | 1421.6 | 1061.0 | 1064.2 | 1179.2 | 1064.3 | 1296.2 |
| 1262.9 | 1487.8 | 1140.9 | 1079.2 | 1202.3 | 1112.2 | 1322.2 |
| 1293.9 | 1504.9 | 1158.0 | 1107.1 | 1235.1 | 1154.1 | 1361.3 |
| 1377.9 | 1527.8 | 1180.1 | 1149.1 | 1277.3 | 1179.2 | 1394.1 |
| 1391.0 | 1797.8 | 1208.0 | 1179.2 | 1296.1 | 1201.2 | 1407.1 |
| 1533.8 | 2161.6 | 1278.0 | 1188.1 | 1300.1 | 1235.1 | 1493.2 |
| 1617.8 | 2178.6 | 1299.9 | 1235.1 | 1307.2 | 1243.2 | 1512.2 |
| 1741.7 | 2216.5 | 1307.0 | 1277.2 | 1361.2 | 1296.1 | 1535.2 |

TABLE 3-continued

Peptide masses obtained by MALDI-MS of seven proteins excised from 2-D gels and digested with trypsin.

| FLB-1 52 | FLB-2 48 | FLB-3 52 | FLB-4 48 | FLB-5 42 | FLB-6 42 | FLB-7 38 |
|---|---|---|---|---|---|---|
| 1769.8 | 2233.4 | 1383.9 | 1308.1 | 1407.1 | 1361.2 | 1553.1 |
| 1792.7 | 2272.6 | 1486.9 | 1391.3 | 1475.2 | 1397.0 | 1585.1 |
| 1938.3 | 2726.2 | 1583.8 | 1406.1 | 1488.2 | 1407.1 | 1618.3 |
| 2025.57 |  | 1638.9 | 1475.1 | 1552.1 | 1497.0 | 1729.1 |
| 2151.5 |  | 1698.9 | 1487.1 | 1585.1 | 1512.1 | 1774.2 |
| 2457.4 |  | 1715.8 | 1534.1 | 1619.2 | 1535.0 | 1792.0 |
|  |  | 1738.8 | 1618.1 | 1638.2 | 1551.2 | 1970.2 |
|  |  | 1791.6 | 1715.9 | 1699.1 | 1585.1 | 2180.1 |
|  |  | 1844.7 | 1770.1 | 1717.1 | 1618.2 | 2383.8 |
|  |  | 1993.7 | 1791.0 | 1729.0 | 1729.1 | 2596.8 |
|  |  | 2162.5 | 1914.0 | 1791.0 | 1756.0 |  |
|  |  | 2179.6 | 1993.6 | 1838.1 | 1775.0 |  |
|  |  | 2221.8 | 2025.9 | 1994.1 |  |  |
|  |  | 2238.4 | 2151.8 | 2181.0 |  |  |
|  |  | 2383.0 |  | 2383.9 |  |  |
|  |  | 2704.7 |  | 2412.0 |  |  |
|  |  | 2717.2 |  | 2703.8 |  |  |
|  |  | 2854.0 |  | 2706.9 |  |  |
|  |  | 3041.7 |  |  |  |  |

TABLE 4

Mass correlation of FLB-1 derived tryptic peptides, soybean beta-conglycinin, alpha chain precursor.

| Observed M/z | Matched MH+ | Residues | Peptide Sequence |
|---|---|---|---|
| 564.23 | 564.28 | 220-223 | (R)FNQR(S) (SEQ ID NO: 2) |
| 564.23 | 564.31 | 393-397 | (K)SSSRK(T) (SEQ ID NO: 3) |
| 621.3 | 621.37 | 356-360 | (K)VLFSR(E) (SEQ ID NO: 4) |
| 859.3 | 859.46 | 279-286 | (R)LQSGDALR(V) (SEQ ID NO: 5) |
| 955.27 | 955.53 | 224-231 | (R)SPQLQNLR(D) (SEQ ID NO: 6) |
| 1079.2 | 1079.54 | 410-418 | (R)SRDPIYSNK(L) (SEQ ID NO: 7) |
| 1188.12 | 1188.52 | 361-370 | (R)EEGQQQGEQR(L) (SEQ ID NO: 8) |
| 1308.18 | 1308.72 | 419-429 | (R)LGKFFEITPEK(N) (SEQ ID NO: 9) |
| 1391.32 | 1391.62 | 47-57 | (R)DSYRNQACHAR(C) (SEQ ID NO: 10) |
| 1391.32 | 1391.87 | 306-318 | (R)LITLAIPVNKPGR(F) (SEQ ID NO: 11) |
| 1406.18 | 1406.72 | 398-409 | (K)TISSEDKPFNLR(S) (SEQ ID NO: 12) |
| 1534.18 | 1534.82 | 397-409 | (R)KTISSEDKPFNLR(S) (SEQ ID NO: 13) |
| 1618.17 | 1618.85 | 422-434 | (K)FFEITPEKNPQLR(D) (SEQ ID NO: 14) |
| 1770.13 | 1770.99 | 371-385 | (R)LQESVIVEISKEQIR(A) (SEQ ID NO: 15) |
| 1791.09 | 1790.87 | 356-370 | (K)VLFSREEGQQQGEQR(L) (SEQ ED NO: 16) |
| 1914.0 | 1913.94 | 340-355 | (R)NILEASYDTKFEEINK(V) (SEQ ID NO: 17) |
| 2025.9 | 2025.94 | 479-494 | (K)EQQQEQQQEEQPLEVR(K) (SEQ ID NO: 18) |
| 2151.88 | 2152.03 | 287-305 | (R)VPSGTTYYVVNPDNNENLR(L) (SEQ ID NO: 19) |

A peptide mass fingerprint for FLB-4 obtained 16 of 24 tryptic peptide matches to a protein known as soybean beta-conglycinin, beta chain precursor (Table 5, NCBInr5.13.99 database). This suggests that both the alpha and beta chain precursor proteins have been identified for soybean beta-conglycinin.

TABLE 5

Mass correlation of FLB-4 derived tryptic peptides, soybean beta-conglycinin, beta chain precursor.

| Observed M/z | Matched MH+ | Residues | Peptide Sequence |
|---|---|---|---|
| 545.0 | 545.3 | 216-219 | (K)EQIR(Q) (SEQ ID NO: 20) |
| 545.0 | 545.3 | 383-386 | (R)QIER(Q) (SEQ ID NO: 21) |
| 564.0 | 564.3 | 59-62 | (R)FNKR(S) (SEQ ID NO: 22) |
| 564.0 | 564.3 | 227-231 | (K)SSSRK(T) (SEQ ID NO: 23) |
| 659.0 | 659.3 | 220-224 | (R)QLSRR(A) (SEQ ID NO: 24) |
| 956.0 | 956.5 | 63-70 | (R)SPQLENLR(D) (SEQ ID NO: 25) |
| 1064.4 | 1064.6 | 148-157 | (K)LAIPVNKPGR(Y) (SEQ ID NO: 26) |
| 1112.0 | 1112.6 | 62-70 | (K)RSPQLENLR(D) (SEQ ID NO: 27) |
| 1235.3 | 1235.5 | 195-204 | (R)VLFGEEEEQR(Q) (SEQ ID NO: 28) |
| 1361.0 | 1361.7 | 371-382 | (R)NFLAGEKDNVVR(Q) (SEQ ID NO: 29) |
| 1407.0 | 1407.6 | 232-243 | (K)TISSEDEPFNLR(S) (SEQ ID NO: 30) |
| 1512.0 | 1512.7 | 318-329 | (K)QKQEEEPLEVQR(Y) (SEQ ID NO: 31) |
| 1535.0 | 1535.7 | 231-243 | (R)KTISSEDEPFNLRS(S) (SEQ ID NO: 32) |
| 1585.0 | 1585.7 | 26-37 | (K)VREDENNPFYFR(S) (SEQ ID NO: 33) |
| 1618.0 | 1618.8 | 256-268 | (K)FFEITPEKNPQLR(D) (SEQ ID NO: 34) |
| 1774.2 | 1773.8 | 387-402 | (R)QVQELAFPGSAQDVER(L) (SEQ ID NO: 35) |
| 2180.0 | 2181.1 | 126-144 | (R)IPAGTTYYLVNPHDHQNLK(I) (SEQ ID NO: 36) |
| 2596.85 | 2597.2 | 103-125 | (R)AILTLVNNDDRDSYNLHPGDAQR(I) (SEQ ID NO: 37) |

The above peptide mass fingerprints (FLB-1 to FLB-7) may be used to identify each protein marker, which when resolved on a 2-D gel illustrates a unique protein pattern. Thus, the protein pattern may be used to detect the presence or absence of EPSPS (EP-1), according to the methods described within the invention. It is appreciated that the skilled artisan, in view of the foregoing disclosure, would be able to produce nucleic acid sequences which encode the fragments described above, as well as nucleic acid sequences complementary thereto. In addition, the skilled artisan using conventional recombinant DNA methodologies, for example, by screening a cDNA library with such a nucleic acid sequence, would be able to isolate full length nucleic acid sequences encoding marker proteins.

EXAMPLE 4

Identification of
5-enolpyruvylshikimate-3-phosphate Synthase in
Transgenic Soybean Leaves Isolation of 5-enolpyruvylshikimate-3-phosphate synthase from transgenic soybean leaves.

A comparison of Coomassie stained SDS-PAGE gel patterns of proteins isolated from transgenic and non-transformed soybean leaf tissue resulted in the identifiction of EPSPS protein. Fresh leaf tissue was harvested from soybean plants 14-17 days after germination in a controlled environmental chamber and stored at −80° C. until further processing. Three leaves were sliced into small (2 mm) pieces and homogenized with a mortar and pestle on dry ice and treated with a buffered solution containing 100 mM Tris HCl, pH 7.8, 5 mM magnesium chloride, 100 mM sodium borate, 0.2% sodium ascorbate, and 0.05% v/v Tween 80. The homogenate was transferred to a 1.5 mL microfuge tube, sonicated for 5 min., and transferred to ice for 10 min. This procedure was repeated twice. Insoluble cellular debris was removed by centrifuging the homogenate for 10 min. at 14,000 g. The supernatant was transferred to a clean 1.5 mL microfuge tube. The Bio-Rad Protein Assay kit using a bovine gamma globulin standard was used to determine the protein concentration of the supernatant.

The resulting soluble proteins were subjected to high-resolution SDS-PAGE analysis. Gel electrophoresis was performed according to standard procedures. Criterion™ precast 1 mm thick 4-20% gradient Tris-HCl gels (Bio-RAD, Hercules, Calif.) were used throughout, although gels with other acrylamide concentrations, thicknesses and numbers of wells can be used, depending on the desired molecular mass range, and sample volumes. Electrophoresis was carried out on a Criterion mini electrophoresis cell (Bio-RAD) at room temperature. The electrophoresis running buffer was prepared from a 10X Tris-glycine-SDS solution (Bio-RAD). Following assembly of the gel system and addition of the running buffer, the soluble proteins were denatured in a Laemmli Sample Buffer (Bio-Rad) by boiling for 2 min. The protein/sample buffer solutions were vortexed and centrifuged prior to loading onto the gel. Electrophoresis was carried out at an initial current of 35 mA using a EC 105 power supply and was terminated when the dye front reached the bottom of the gel. Typical run times were 1.5 h. Molecular weight standards consisted of myosin ($M_r$ 205,000), β-galactosidase ($M_r$ 120,000), bovine serum albumin ($M_r$ 84,000), ovalbumin ($M_r$ 52,200), carbonic anhydrase ($M_r$ 36,300), soybean trypsin inhibitor ($M_r$ 30,200), lysozyme ($M_r$ 21,900), and aprotinin ($M_r$ 7,400) (Bio-Rad). Following electrophoresis, gels were stained in 0.2% Coomassie Brillant Blue G-250 and destained 5-enolpyruvylshikimate-3-phosphate synthase (EPSPS) was identified by SDS-PAGE.

As described in the previous above, SDS-PAGE was obtained by separating and resolving proteins isolated from either non-transformed or transgenic soybean leaves expressing EPSPS. FIG. 2 shows a SDS-PAGE gel displaying proteins from a typical protein pattern by transgenic soybean leaves expressing EPSPS.

Figure 4:
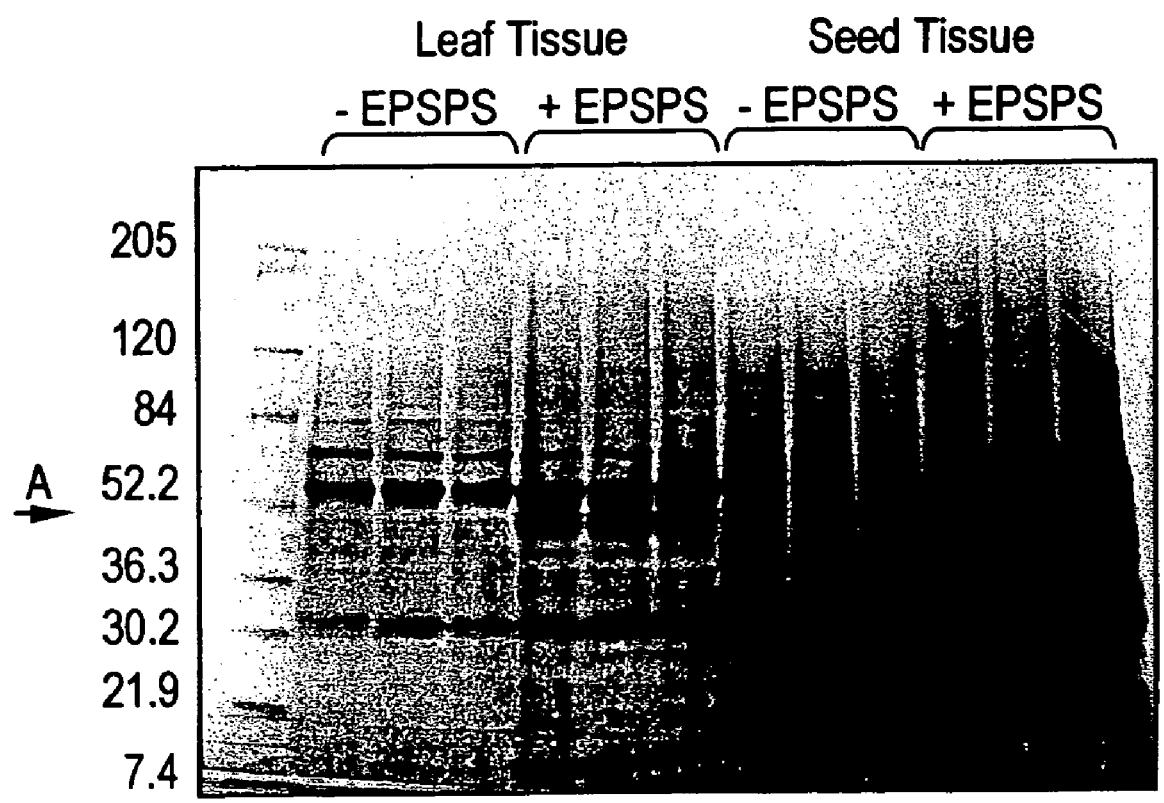
FIG. 4 is a photograph of an SDS-PAGE Commassie stained gel with different lanes of soybean leaf and seed tissue with the absence and presence of EPSPS, wherein the arrow (→) indicates location of EPSPS.

Comparison of protein patterns (FIG. 4) reveals that, while most proteins in the non-transformed and transformed soybean leaves are identical, one protein having a molecular weight of approximately 48 kDa is unique to the transgenic soybean leaf samples (labeled in FIG. 4). The protein labeled EPleaf-1 was reproducibly detected in all samples analyzed which had been previously identified as being transgenic for EPSPS.

Characterization and Identification of EPleaf-1

One protein band corresponding to EPleaf-1 was excised, proteolytically cleaved, and analyzed by mass spectrometry as described herein. Using the methodology described above, EPleaf-1 (MW 48 kDa) was isolated from 2-3 lanes on a SDS-PAGE gel of transgenic soybean seeds encoding the EPSPS gene, digested with trypsin, and the peptides were extracted. The resulting peptide mixture was analyzed directly by MALDI-MS. Correlation of the determined masses with the EPSPS sequence is shown in Table 6. Sixteen diagnostic tryptic peptide masses were identified, which covers 53% of the EPSPS sequence.

TABLE 6

Peptide masses obtained by MALDI-MS of the 48 kDa
EPleaf-1 protein band digested with trypsin.

| Observed M + H | Predicted M | Sequence | Residues of SEQ ID NO: 1 |
|---|---|---|---|
| 616.2 | 615.8 | RPMGR | 128-132 |
| 711.2 | 710.9 | VLNPLR | 133-138 |
| 832.3 | 832.0 | MSHGASSR | 1-8 |
| 835.2 | 835.0 | AMQAMGAR | 62-69 |
| 862.1 | 862.9 | GLSGTVR | 15-23 |
| 872.1 | 872.0 | SAVANGLK | 358-366 |
| 872.0 | 871.9 | GVTVPEDR | 313-320 |
| 948.1 | 948.1 | TPTPITYR | 161-168 |
| 1115.0 | 1115.2 | LAGGEDVADLR | 295-305 |
| 1358.9 | 1359.5 | SFMFGGLASGETR | 34-46 |

TABLE 6-continued

Peptide masses obtained by MALDI-MS of the 48 kDa
EPleaf-1 protein band digested with trypsin.

| Observed M + H | Predicted M | Sequence | Residues of SEQ ID NO: 1 |
|---|---|---|---|
| 1464.9 | 1465.2 | EMGVQVKSEDGDR | 139-151 |
| 1645.9 | 1646.8 | GLGNASGAAVATHLDHR | 389-405 |
| 1993.7 | 1994.2 | MLQGFGANLTVETDADGVR | 206-224 |
| 2182.6 | 2183.5 | TGLILTLQEMGADIEVINPR | 275-294 |
| 2366.6 | 2367.8 | SAVLLAGLNTPGITTVIEPIMTR | 178-200 |
| 3250.2 | 3250.7 | APSMIDEYPILAVAAAFAEGATVMNGLEELR | 321-351 |
| 4190.2 | 4189.9 | LTGQVIDVPGDPSSTAFPLVAALLVPGSDVTILNVLMNPTR | 234-274 |

*underlining reflects sequences confirmed by MALDI-PSD.

Sequence tags were obtained from EPleaf-1 to definitively identify the protein by mass spectrometry. Post source decay (PSD) fragment ion spectra were acquired for five peptides (832.3, 1358.9, 1646.8, 1993.7, and 2182.6 m/z) after isolation of the appropriate precursor ion by using timed ion selection. Fragment ions were refocused as described herein. The individual segments were stitched together by using software provided by PerSeptive Biosystems. The MALDI-PSD analysis verified the amino acid sequence for each of the five-peptide masses.

EXAMPLE 5

Detection and Quantification of 5-enolpyruvylshikimate-3-phosphate synthase in Soybean Tissue Method to enrich for EPSPS in plant tissue.

Once EPSPS was identified in both seed and leaf tissue, a method to enrich for EPSPS was employed to assist rapid detection and quantification of the target protein from plant tissue. All protein enrichment procedures were carried out on ice. EPSPS isolation from leaf and seed were done as previously described herein, except the extraction buffer consisted of 100 mM Tris HCl, pH 7.8, 5 mM magnesium chloride, 100 mM sodium borate, and 0.2% sodium ascorbate. The slurry was transferred to a 2 mL Kontes glass tissue grinder for further homogenization. The homogenate was transferred to a 1.5 mL microfuge tube, sonicated for 5 min., and chilled on ice for 10 minutes. This procedure was repeated twice. Insoluble cellular debris was removed by centrifuging the homogenate for 10 min. at 14,000 g. The supernatant was decanted into a clean 1.5 mL microfuge tube. The Bio-Rad Protein Assay kit using a bovine gamma globulin standard was used to determine the protein concentration of the supernatant.

The resulting soluble proteins were loaded onto 200 μL of equilibrated Q-Sepharose resin in a 1.5 mL microfuge tube and gently inverted several times for 10 minutes. Q-Sepharose resin and protein complexes were centrifuged at 3,000 g for 10 seconds. Unbound soluble proteins were removed by washing with 3 volumes of buffer. In 100 mM increments, starting with 100 mM NaCl to 1,000 mM NaCl the resins were washed with each salt concentration to fractionate proteins. Each fraction was collected and analyzed by SDS-PAGE, followed by excising, proteolytic cleaving, and analyzing by MALDI-TOF MS. Peptide mass fingerprints were used to verify the presence or absence of EPSPS in the various tissues.

EPSPS eluted from fractions washed with 300-400 mM NaCl.

The resulting enrichment of EPSPS was found to be nearly 50% of the protein from leaf and 10% of the protein from seed.

Use of modified peptides for detection and quantification of EPSPS.

It is possible to use MALDI-TOF MS to analyze any compound in a sample after the analytes of interest have been extracted from a sample matrix. Key issues include the selection of matrixes, preparation of matrix and sample, signal-to-noise ratio, spot-to-spot reproducibility, and response factors. Because of spot-to-spot variation, an internal standard is a requirement for quantification of analytes using MALDI-TOF MS. In this example, two EPSPS tryptic peptides were selected for internal standards. Several criteria were used to select the two peptides. First, the two peptides needed to be located near the C-terminal and N-Terminal of EPSPS, this would allow for the monitoring of protein processing. The second requirement is that both peptides need to be detected under lower laser strength with good spot-to-spot reproducibility and high sensitivity. Third, each peptide needed to be modified such that the peptide mass was not overlapping the native peptide mass (precursor peptide mass) and/or other signature or non-signature diagnostic peptides. The fourth requirement was to have peptides, which could easily be synthesized. Two peptides were selected from the peptide mass fingerprints from EPSPS isolated from seed and leaf as described herein, which met the above criteria (Table 7).

TABLE 7

Selected peptides for monitoring and quantifying EPSPS.

| Sequence | Residues of SEQ ID NO: 1 | Mass | Modification (acetylation) | Modified peptide mass |
|---|---|---|---|---|
| MP-1 SFMFGGLASGETR | 34-46 | 1359.5 | 42 | 1401.5 |
| MP-2 GLGNASGAAVATHLDHR | 389-405 | 1646.8 | 42 | 1688.8 |

Both peptides were synthesized by solid phase and the N-terminal of each peptide was modified by acetylation (Genemed Synthesis Inc, South San Francisco, Calif.). This modification increases the mass of each peptide by 42 Da (Table 7).

leaf material no peptides corresponding to EPSPS were identified. In each of the transformed lines with EPSPS signature diagnostic peptide masses were detected. It should be noted that this example provided the ability to detect signature diagnostic peptide masses as a means to monitor for EPSPS.

TABLE 8

Screening for diagnostic peptide mass fingerprints of EPSPS in soybean leaf tissue.

| Sample | Diagnostic peptide masses m/z | | | | | | | | | |
|---|---|---|---|---|---|---|---|---|---|---|
| | 616 | 711 | 862 | 1115 | 1358 | 1645 | 1993 | 2182 | 2366 | 3256 |
| Control | − | − | − | − | − | − | − | − | − | − |
| SLP-1 | + | + | + | + | + | + | + | + | + | + |
| SLP-2 | + | + | + | + | + | + | + | + | + | + |
| SLP-3 | + | + | + | + | + | + | + | + | + | + |
| SLP-4 | + | + | + | + | + | + | + | + | + | + |
| SLP-5 | + | + | + | + | + | + | + | + | + | + |
| SLP-6 | + | + | + | + | + | + | + | + | + | + |
| SLP-7 | + | + | + | + | + | + | + | + | + | + |
| SLP-8 | + | + | + | + | + | + | + | + | + | + |
| SLP-9 | + | + | + | + | + | + | + | + | + | + |

+ = presence of peptide mass,
− = absence of peptide mass

Calibration Curve Construction

Figure 5A:
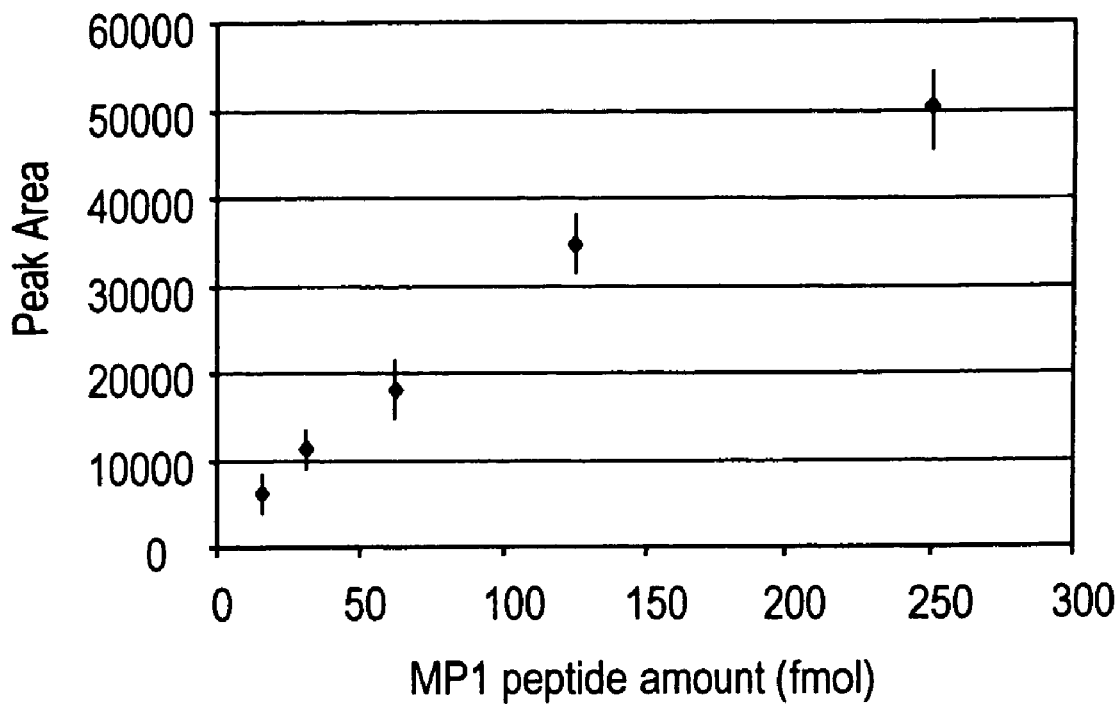
FIGS. 5A and B are graphs of calibration curves for (A) synthetic modified peptide MP-1 and (B) synthetic modified peptide MP-2.
Figure 5B:
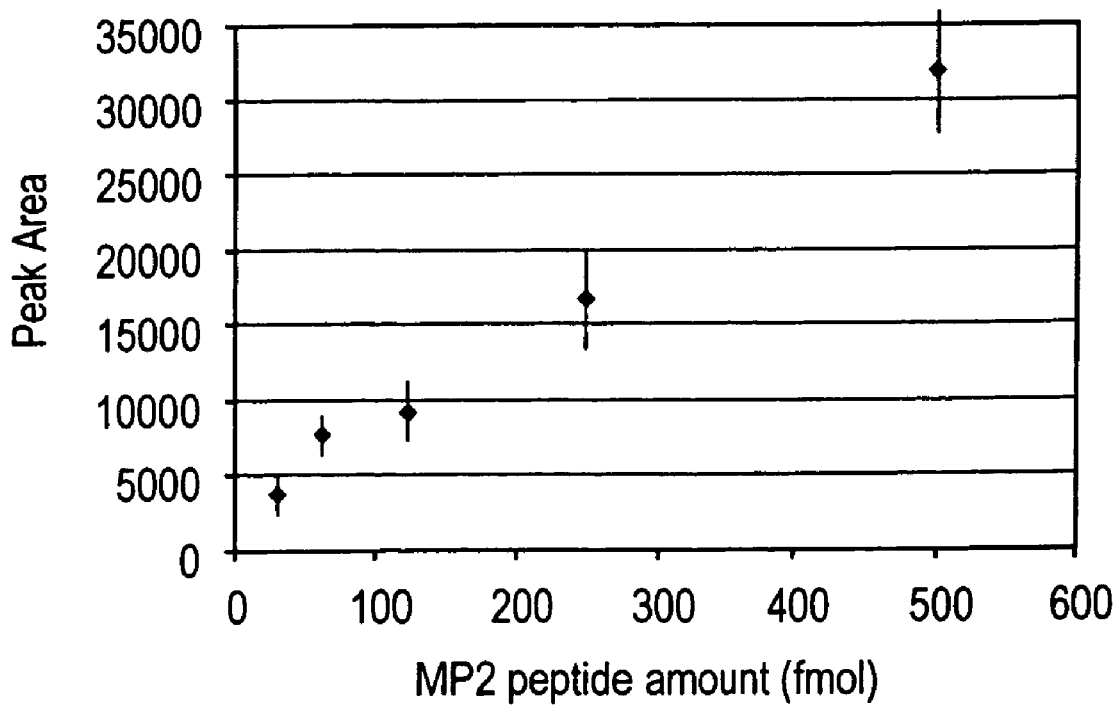

To establish the detection sensitivity, calibration curves for each peptide were constructed using known amounts of the two synthetic peptides. Various concentrations of peptide solutions were prepared and subjected MALDI-TOF MS analysis. Synthetic peptides were analyzed at amounts ranging from 15.6 fmol, 31.2 fmol, 62.5 fmol, 125 fmol, 250 fmol, and 500 fmol for both peptides. Calibration curves were also validated with spiked modified peptides in plant extracts or enriched target proteins. Various concentrations of peptide solutions were prepared and analyzed blind by MALDI-TOF MS. All calibration points were examined in triplicate and a linear correlation was observed for both peptides over this concentration range (FIGS. 5A and 5B). These blind tests demonstrated the inter-run reproducibility of the calibration curves. The results demonstrate levels of detection below 10 femtomoles.

Rapid Screening of EPSPS in Soybean Leaf Tissue

Figure 6A:
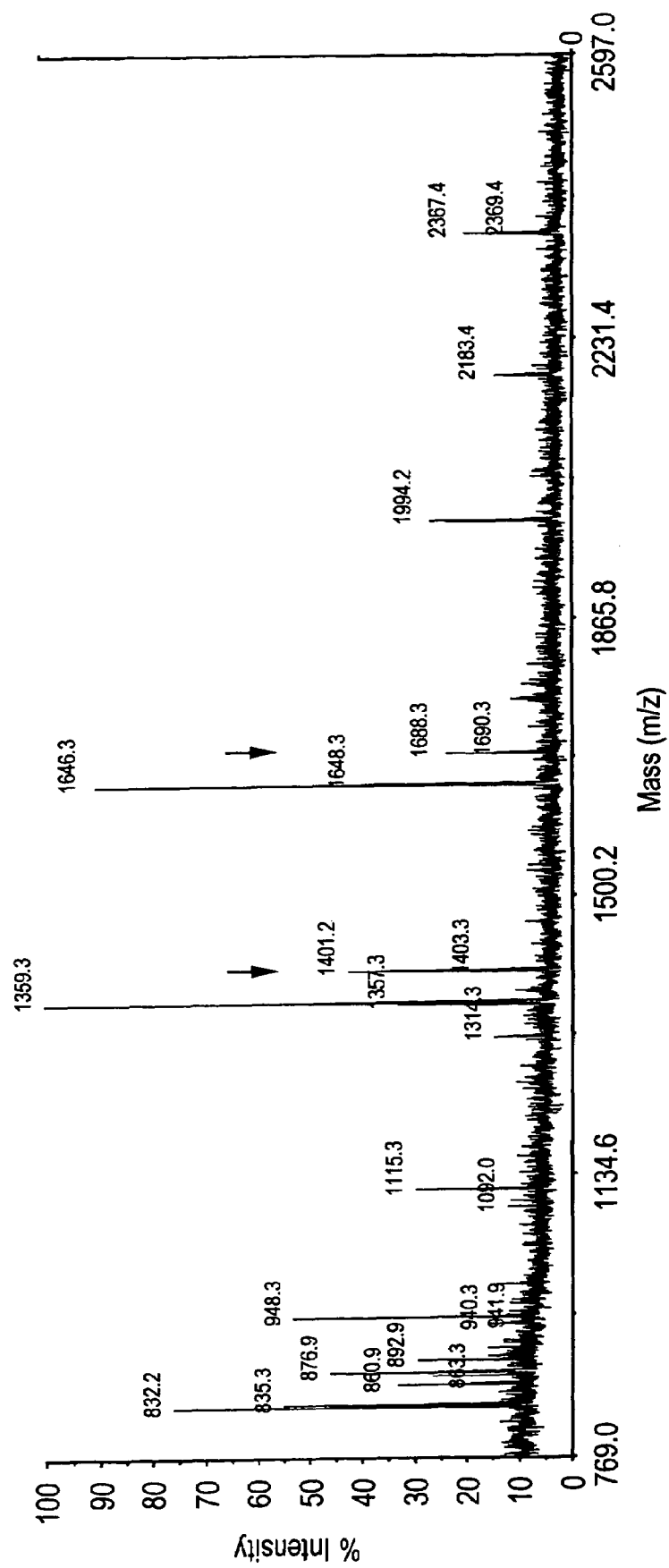
Figure 6B:
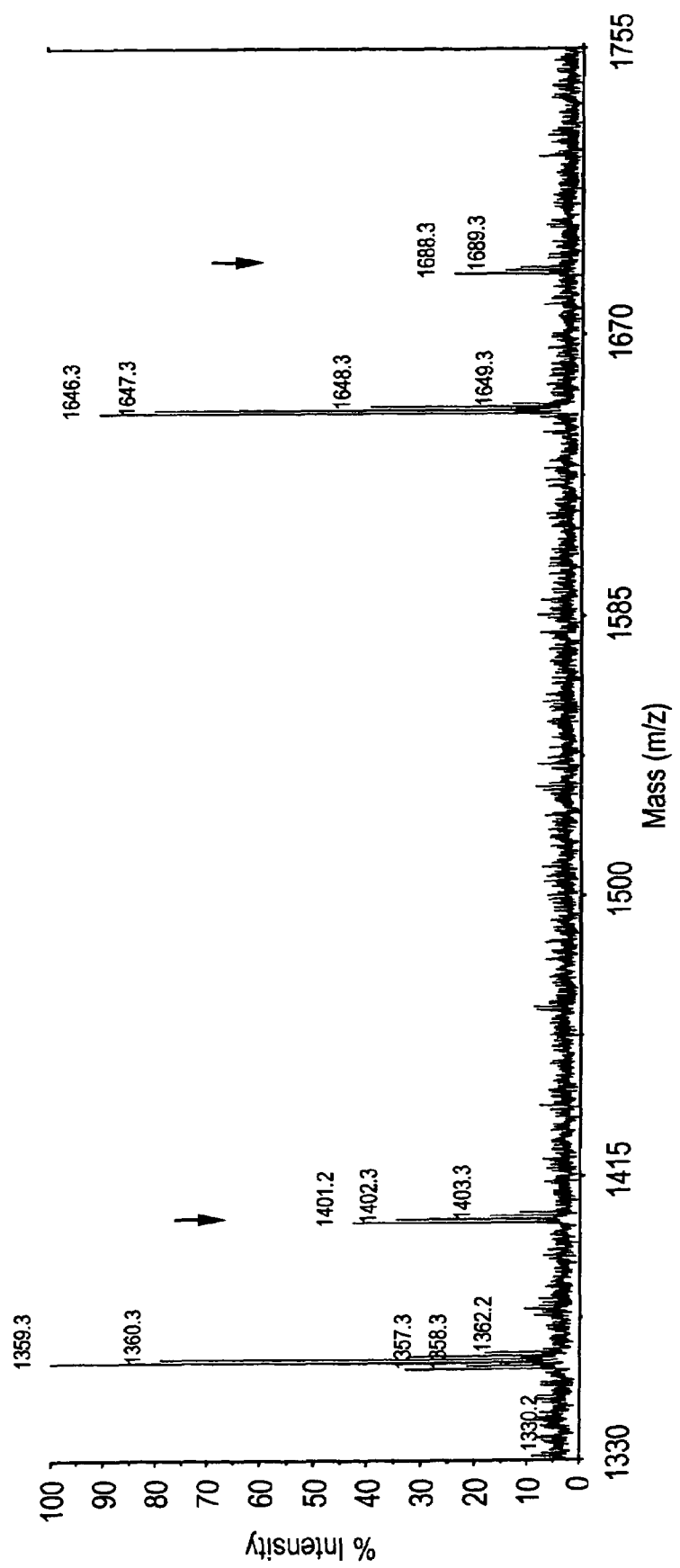
FIG. 6B shows calibrants with parent peaks, and wherein arrows (↓) indicate calibrants MP-1=1401.2 m/z and MP-2=1688.3.

The techniques of the present invention were used to monitor for the expression of EPSPS in soybean leaf tissue. Ten different soybean plants were grown; one plant that did not express EPSPS was used as a control. Plant tissue was homogenized as described herein and 50 μg of total protein were loaded onto SDS-PAGE. A corresponding protein at a molecular weight of 48 kDa was excised, proteolytically cleaved with trypsin, and analyzed by MALDI-TOF MS. In Table 8, diagnostic peptide masses were identified in soybean leaf tissue from nine distinct samples. In the control soybean Quantitation of EPSPS from a SDS-PAGE On the basis of the high sensitivity achieved for MALDI-TOF MS in the detection of EPSPS a protein at 48 kDa was excised from SDS-PAGE, and the method was used as an alternative technique to quantify EPSPS in soybean tissues of both seeds and leaves. Modified-peptides were added to "in-gel" tryptic peptides used as internal calibrants for monitoring, detecting, and quantifying EPSPS (FIGS. 6A and 6B). Tables 9 and 10 list the EPSPS content of 6 soybean leaf samples and Table 11 lists the EPSPS content of 10 soybean seed samples as determined by MALDI-TOF MS analysis. Five soybean leaf samples and nine soybean seed samples had EPSPS peptide masses which allowed quantification within the linear range. Two of the samples did not result in the detection of EPSPS peptide masses.

TABLE 9

MALDI-TOF MS quantification of EPSPS in soybean leaves from separation from SDS-PAGE using MP-1 spiked calibrant.

| Sample | 1359 (mean) | Spike 1401 (mean) | Ratio | MP-1 (fmol) | EPSPS (fmol) |
|---|---|---|---|---|---|
| Leaf 1 | 51652 | 18964 | 2.7 | 250 | 681 |
| Leaf 2 | 70638 | 13848 | 5.1 | 250 | 1275 |
| Leaf 3 | 55013 | 13371 | 4.1 | 250 | 1028 |
| Leaf 4 | 32147 | 11340 | 2.8 | 250 | 708 |
| Leaf 5 | 60520 | 11847 | 5.1 | 250 | 1277 |

TABLE 10

MALDI-TOF MS quantification of EPSPS in soybean leaves from separation from SDS-PAGE using MP-2 spiked calibrant.

| Sample | 1646 (mean) | Spike 1688 (mean) | Ratio | MP-2 (fmol) | EPSPS (fmol) |
|---|---|---|---|---|---|
| Leaf 1 | 41369 | 9723 | 4.2 | 250 | 1050 |
| Leaf 2 | 28429 | 6800 | 4.2 | 250 | 1050 |
| Leaf 3 | 30466 | 7377 | 4.1 | 250 | 1025 |
| Leaf 4 | 21970 | 4788 | 4.6 | 250 | 1150 |
| Leaf 5 | 29338 | 5338 | 5.5 | 250 | 1375 |

TABLE 11

MALDI-TOF MS quantification of EPSPS in soybean seeds from separation from SDS-PAGE using MP-1 spiked calibrant.

| Sample | 1359 (mean) | Spike 1401 (mean) | Ratio | MP-1 (fmol) | EPSPS (fmol) |
|---|---|---|---|---|---|
| Seed 1 | 33828 | 17534 | 1.9 | 250 | 475 |
| Seed 2 | 22158 | 23664 | 0.94 | 250 | 235 |
| Seed 3 | 21743 | 21214 | 1.02 | 250 | 255 |
| Seed 4 | 13657 | 20394 | 0.67 | 250 | 167.5 |
| Seed 5 | 16257 | 19216 | 0.85 | 250 | 212.5 |
| Seed 6 | 17439 | 22830 | 0.76 | 250 | 190 |
| Seed 7 | 15441 | 21434 | 0.72 | 250 | 180 |
| Seed 8 | 11496 | 19764 | 0.58 | 250 | 145 |
| Seed 9 | 12226 | 18069 | 0.68 | 250 | 170 |

Quantitation of EPSPS in Soybean Leaves

All soybean leaves samples were analyzed using the resin-developed method. MP-1 and MP-2 were used as an internal calibrants and added to the enriched EPSPS tryptic digest. The results are presented in Tables 12 and 13. These data indicate that MALDI-TOF MS coupled with a resin-based method accurately determined EPSPS levels in soybean leaves.

TABLE 12

MALDI-TOF MS quantification of EPSPS in soybean leaves after enriching by Q-Sepharose resin using MP-1 spiked calibrant.

| Sample | 1359 (mean) | Spike 1401 (mean) | Ratio | MP-1 (fmol) | EPSPS (fmol) |
|---|---|---|---|---|---|
| Leaf 1 | 38248 | 14469 | 2.64 | 250 | 661 |
| Leaf 2 | 20571 | 8757 | 2.35 | 250 | 587 |
| Leaf 3 | 46781 | 14824 | 3.16 | 250 | 789 |
| Leaf 4 | 32040 | 9560 | 3.35 | 250 | 838 |
| Leaf 5 | 24204 | 12500 | 1.94 | 250 | 484 |

TABLE 13

MALDI-TOF MS quantification of EPSPS in soybean leaves after enriching by Q-Sepharose resin using MP-2 spiked calibrant.

| Sample | 1646 (mean) | Spike 1688 (mean) | Ratio | MP-2 (fmol) | EPSPS (fmol) |
|---|---|---|---|---|---|
| Leaf 1 | 24667 | 7157 | 3.45 | 250 | 861 |
| Leaf 2 | 17196 | 5602 | 3.07 | 250 | 767 |
| Leaf 3 | 15202 | 4638 | 3.28 | 250 | 819 |
| Leaf 4 | 20469 | 6598 | 3.10 | 250 | 775 |
| Leaf 5 | 22369 | 7953 | 2.81 | 250 | 703 |

EXAMPLE 6

Detection and Quantification of 5-enolpyruvylshikimate-3-phosphate Synthase in Maize Tissue As demonstrated in previous examples, EPSPS can be quantified in different dicot tissues such as seed and leaves. However the method is readily applicable to other plant species. Therefore, samples of leaf samples from maize (a monocot plant) were analyzed using the resin-developed method developed for soybean leaves. MP-1 was used as an internal calibrant and added to the enriched EPSPS tryptic digest. The results are presented in Table 14. These data indicate that MALDI-TOF MS coupled with a resin-based method can accurately determine EPSPS levels in maize leaves. The low limit of detection demonstrates the high sensitivity of MALDI-TOF MS for identification of EPSPS.

TABLE 14

MALDI-TOF MS quantification of EPSPS in soybean leaves after enriching by Q-Sepharose resin using MP-1 spiked calibrant.

| Sample | 1359 (mean) | Spike 1401 (mean) | Ratio | MP-1 (fmol) | EPSPS (fmol) |
|---|---|---|---|---|---|
| Leaf 1 | 14848 | 25302 | 0.59 | 250 | 147 |
| Leaf 2 | 11275 | 19858 | 0.57 | 250 | 142 |
| Leaf 3 | 14236 | 23186 | 0.61 | 250 | 153 |
| Leaf 4 | 18018 | 29271 | 0.61 | 250 | 153 |
| Leaf 5 | 10557 | 18515 | 0.57 | 250 | 142 |

INDUSTRIAL APPLICABILITY

The present invention has applicability in a wide variety of diagnostic applications including quality control.

REFERENCED PUBLICATIONS

Mann, M., and Wilm, M., Anal. Chem. 66: 4390-4399 (1994).
Yates, J. R., Eng, J. K., McCormack, A. L. and Schieltz, D., Anal. Chem. 67(8): 1426-36 (1995).
Boucherie, H., Sagliocco, F., Joubert, R., Maillet, I., Labarre, J., and Perrot, M., Electrophoresis 17(11): 1683-99 (1996).
Aebersold, R., Rist, B., Gygi, S. P., Ann. N. Y. Acad. Sci. 919:33-47 (2000).
Gygi, S. P., Rist, B., Gerber, S. A., Turecek, F., Gelb, M., and Aebersold, R., Nat. Biotech. 17(10): 994-999 (1999).
Munchbach, M., Quodroni, M., Miotto, G., and James, P., Anal. Chem. 72(17): 4047-57 (2000).

All patent and non-patent publications cited in this specification are indicative of the level of skill of those skilled in the art to which this invention pertains. All these publications and patent applications are herein incorporated by reference to the same extent as if each individual publication or patent application was specifically and individually indicated as being incorporated by reference herein. In addition, the entirety of commonly owned international application no., PCT/US02/12012 entitled "DETECTION AND QUANTIFICATION OF PRION ISOFORMS 1N NEUROGENERATIVE DISEASES USING MASS SPECTROMETRY" filed Apr. 17, 2002, is incorporated herein by reference.

Those skilled in the art will recognize, or be able to ascertain, using no more than routine experimentation, numerous equivalents to the specific substances and procedures described herein. Such equivalents are considered to be within the scope of this invention.

The invention claimed is:

1. A method of detecting a target protein in a biological sample, comprising:
   (a) obtaining a biological sample;
   (b) extracting proteins from the sample;
   (c) concentrating the target protein from extracted proteins of (b), wherein said concentrating comprises contacting extracted proteins of (b) with a first resin that preferentially adsorbs the target protein and a second resin that preferentially absorbs non-target proteins in the sample;

(d) digesting concentrated proteins of (c) to produce peptide fragments of the proteins, wherein the fragments include at least one signature peptide specific to the target protein; and (e) analyzing the peptide fragments via mass spectrometry, wherein detection of the at least one signature peptide is indicative of presence of target protein in the sample.

2. The method of claim 1 wherein said method further comprises (i) introducing an internal standard peptide corresponding to said at least one signature peptide prior to (e) and (ii) calculating amount of the protein in the sample by comparing mass spectrometry signals generated from the signature peptide and its corresponding internal standard peptide in said step (e).

3. The method of claim 2 wherein said digesting produces peptide fragments containing at least two signature peptides and said method further comprises (i) introducing an internal standard peptide corresponding to at least one of said at least two signature peptides prior to (e) and (ii) comparing mass spectrometry signals generated from said at least one of the at least two signature peptides and its corresponding internal standard peptide in (e).

4. The method of claim 1 wherein the sample is a plant or derived from a plant.

5. The method of claim 4 wherein the sample is plant seed.

6. The method of claim 1 wherein the sample is an animal or derived from an animal.

7. The method of claim 1 wherein the sample is a microorganism or derived from a microorganism.

8. The method of claim 1 wherein the sample is a pharmaceutical or a nutraceutical.

9. The method of claim 1 wherein the sample is a food product or feed.

10. The method of claim 1 wherein the sample is a cosmetic.

11. The method of claim 1 wherein the peptide fragments include at least two signature peptides specific to the target protein.

12. The method of claim 1 wherein the protein is non-native to source of the sample.

13. The method of claim 1 wherein said digesting is performed with a protease which is trypsin, endoprotease-Arg-C, endoprotease-Aspn-N, endoprotease-Glu-C or endoprotease-Lys-C.

14. The method of claim 1 wherein and said analyzing comprises introducing the peptide fragments and a matrix into a matrix assisted laser desorption ionization (MALDI) time-of-flight (TOE) analyzer.

15. The method of claim 14 wherein the matrix comprises alpha-cyano-4-hydroxycinniamic acid.

16. The method of claim 1 wherein said analyzing comprises introducing the peptide fragments into an ion trap electrospray ionization apparatus (ESI)

17. The method of claim 1 further comprising introducing the composition into a liquid chromatograph (LC) prior to said analyzing.

18. The method of claim 17 wherein the LC is a micro-LC.

19. The method of claim 17 wherein the LC is a nano-LC.

20. A method of quantifying a target protein which is an expression product of a transgene contained in a transgenic plant, tissue or cell, or for quantifying the target protein in a product derived from the transgenic plant, comprising:

(a) obtaining a sample from the transgenic plant or the product;
(b) extracting proteins from the sample;
(c) concentrating the target protein from extracted proteins of (b), wherein said concentrating comprises contacting extracted proteins of (b) with a first resin that preferentially adsorbs the target protein and a second resin that preferentially absorbs non-target proteins in the sample;
(d) digesting concentrated proteins of (c) with a protease to produce peptide fragments of the proteins, wherein the fragments include at least one signature peptide specific to the target protein;
(e) analyzing via mass spectrometry the peptide fragments and for at least one signature peptide, a corresponding internal standard peptide; and
(f) calculating amount of the target protein in the sample by comparing mass spectrometry signals generated from the signature peptide with mass spectrometry signals generated by the corresponding internal standard peptide.

21. A method of quantifying a target protein which is an expression product of a transgene contained in a transgenic animal, tissue or cell, or for quantifying the target protein in a product derived from the transgenic animal, comprising:

(a) obtaining a sample from the transgenic animal or the product;
(b) extracting proteins from the sample;
(c) concentrating the target protein from extracted proteins of (b), wherein said concentrating comprises contacting extracted proteins of (b) with a first resin that preferentially adsorbs the target protein and a second resin that preferentially absorbs non-target proteins in the sample;
(d) digesting concentrated proteins of (c) with a protease to produce peptide fragments of the proteins, wherein the fragments include at least one signature peptide specific to the target protein;
(e) analyzing via mass spectrometry the peptide fragments and for at least one signature peptide, a corresponding internal standard peptide; and
(f) calculating amount of the target protein in the sample by comparing mass spectrometry signals generated from the signature peptide with mass spectrometry signals generated by the corresponding internal standard peptide.

22. A method of quantifying a target protein which is an expression product of a transgene contained in a transgenic microorganism, or for quantifying the target protein in a product derived from the transgenic microorganism, comprising:

(a) obtaining a sample from the transgenic microorganism or the product;
(b) extracting proteins from the sample;
(c) concentrating the target protein from extracted proteins of (b), wherein said concentrating comprises contacting extracted proteins of (b) with a first resin that preferentially adsorbs the target protein and a second resin that preferentially absorbs non-target proteins in the sample;
(d) digesting concentrated proteins of (c) with a protease to produce peptide fragments of the proteins, wherein the fragments include at least one signature peptide specific to the target protein;
(e) analyzing via mass spectrometry the peptide fragments and for at least one signature peptide, a corresponding internal standard peptide; and
(f) calculating amount of the target protein in the sample by comparing mass spectrometry signals generated from the signature peptide with mass spectrometry signals generated by the corresponding internal standard peptide.

23. A method of quantifying a target protein which is an expression product of a transgene contained in a transgenic plant, tissue or cell, or for quantifying the target protein in a product derived from the transgenic plant, comprising:
- (a) obtaining a sample from the transgenic plant or the product;
- (b) extracting proteins from the sample;
- (c) concentrating the target protein from extracted proteins of (b), wherein said concentrating comprises contacting extracted proteins of (b) with a first resin that preferentially adsorbs the target protein and a second resin that preferentially absorbs non-target proteins in the sample;
- (d) digesting concentrated proteins of (c) with a protease to produce peptide fragments of the proteins, wherein the fragments include at least two signature peptide specific to the target protein;
- (e) analyzing via mass spectrometry the peptide fragments and for at least one of the signature peptides, a corresponding internal standard peptide; and
- (f) calculating amount of the target protein in the sample by comparing mass spectrometry signals generated from at least one of the signature peptides with mass spectrometry signals generated by the corresponding internal standard peptide.

24. A method of quantifying a target protein which is an expression product of a transgene contained in a transgenic animal, tissue or cell, or for quantifying the target protein in a product derived from the transgenic animal, comprising:
- (a) obtaining a sample from the transgenic animal or the product;
- (b) extracting proteins from the sample;
- (c) concentrating the target protein from extracted proteins of (b), wherein said concentrating comprises contacting extracted proteins of (b) with a first resin that preferentially adsorbs the target protein and a second resin that preferentially absorbs non-target proteins in the sample;
- (d) digesting concentrated proteins of (c) with a protease to produce peptide fragments of the proteins, wherein the fragments include at least two signature peptide specific to the target protein;
- (e) analyzing via mass spectrometry the peptide fragments and for at least one of the signature peptides, a corresponding internal standard peptide; and
- (f) calculating amount of the target protein in the sample by comparing mass spectrometry signals generated from at least one of the signature peptides with mass spectrometry signals generated by the corresponding internal standard peptide.

25. A method of quantifying a target protein which is an expression product of a transgene contained in a transgenic microorganism, or for quantifying the target protein in a product derived from the transgenic microorganism, comprising:
- (a) obtaining a sample from the transgenic microorganism or the product;
- (b) extracting proteins from the sample;
- (c) concentrating the target protein from extracted proteins of (b), wherein said concentrating comprises contacting extracted proteins of (b) with a first resin that preferentially adsorbs the target protein and a second resin that preferentially absorbs non-target proteins in the sample;
- (d) digesting concentrated proteins of (c) with a protease to produce peptide fragments of the enriched proteins, wherein the fragments include at least two signature peptides specific to the target protein;
- (e) analyzing via mass spectrometry the peptide fragments and for at least one the signature peptides, a corresponding internal standard peptide; and
- (f) calculating amount of the target protein in the sample by comparing mass spectrometry signals generated from at least one of the signature peptides with mass spectrometry signals generated by the corresponding internal standard peptide.

* * * * *

SEQUENCE LISTING

<160> NUMBER OF SEQ ID NOS: 37

<210> SEQ ID NO 1
<211> LENGTH: 455
<212> TYPE: PRT
<213> ORGANISM: Unknown Organism
<220> FEATURE:
<223> OTHER INFORMATION: Description of Unknown Organism: Non-
      transformed or transgenic (EPSPS) amino acid sequence

<400> SEQUENCE: 1

```
Met Ser His Gly Ala Ser Ser Arg Pro Ala Thr Ala Arg Lys Ser Ser
 1               5                  10                  15

Gly Leu Ser Gly Thr Val Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Lys Ala Met Gln
    50                  55                  60

Ala Met Gly Ala Arg Ile Arg Lys Glu Gly Asp Thr Trp Ile Ile Asp
65                  70                  75                  80

Gly Val Gly Asn Gly Gly Leu Leu Ala Pro Glu Ala Pro Leu Asp Phe
                85                  90                  95

Gly Asn Ala Ala Thr Gly Cys Arg Leu Thr Met Gly Leu Val Gly Val
            100                 105                 110

Tyr Asp Phe Asp Ser Thr Phe Ile Gly Asp Ala Ser Leu Thr Lys Arg
        115                 120                 125

Pro Met Gly Arg Val Leu Asn Pro Leu Arg Glu Met Gly Val Gln Val
    130                 135                 140

Lys Ser Glu Asp Gly Asp Arg Leu Pro Val Thr Leu Arg Gly Pro Lys
145                 150                 155                 160

Thr Pro Thr Pro Ile Thr Tyr Arg Val Pro Met Ala Ser Ala Gln Val
                165                 170                 175

Lys Ser Ala Val Leu Leu Ala Gly Leu Asn Thr Pro Gly Ile Thr Thr
            180                 185                 190

Val Ile Glu Pro Ile Met Thr Arg Asp His Thr Glu Lys Met Leu Gln
        195                 200                 205

Gly Phe Gly Ala Asn Leu Thr Val Glu Thr Asp Ala Asp Gly Val Arg
    210                 215                 220

Thr Ile Arg Leu Glu Gly Arg Gly Lys Leu Thr Gly Gln Val Ile Asp
225                 230                 235                 240

Val Pro Gly Asp Pro Ser Ser Thr Ala Phe Pro Leu Val Ala Ala Leu
                245                 250                 255

Leu Val Pro Gly Ser Asp Val Thr Ile Leu Asn Val Leu Met Asn Pro
            260                 265                 270

Thr Arg Thr Gly Leu Ile Leu Thr Leu Gln Glu Met Gly Ala Asp Ile
        275                 280                 285

Glu Val Ile Asn Pro Arg Leu Ala Gly Gly Glu Asp Val Ala Asp Leu
    290                 295                 300

Arg Val Arg Ser Ser Thr Leu Lys Gly Val Thr Val Pro Glu Asp Arg
305                 310                 315                 320

Ala Pro Ser Met Ile Asp Glu Tyr Pro Ile Leu Ala Val Ala Ala Ala
                325                 330                 335

Phe Ala Glu Gly Ala Thr Val Met Asn Gly Leu Glu Glu Leu Arg Val
```

-continued

```
               340                 345                 350
Lys Glu Ser Asp Arg Leu Ser Ala Val Ala Asn Gly Leu Lys Leu Asn
        355                 360                 365

Gly Val Asp Cys Asp Glu Gly Glu Thr Ser Leu Val Val Arg Gly Arg
    370                 375                 380

Pro Asp Gly Lys Gly Leu Gly Asn Ala Ser Gly Ala Ala Val Ala Thr
385                 390                 395                 400

His Leu Asp His Arg Ile Ala Met Ser Phe Leu Val Met Gly Leu Val
                405                 410                 415

Ser Glu Asn Pro Val Thr Val Asp Ala Thr Met Ile Ala Thr Ser
            420                 425                 430

Phe Pro Glu Phe Met Asp Leu Met Ala Gly Leu Gly Ala Lys Ile Glu
        435                 440                 445

Leu Ser Asp Thr Lys Ala Ala
        450                 455

<210> SEQ ID NO 2
<211> LENGTH: 6
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 2

Arg Phe Asn Gln Arg Ser
1               5

<210> SEQ ID NO 3
<211> LENGTH: 7
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 3

Lys Ser Ser Ser Arg Lys Thr
1               5

<210> SEQ ID NO 4
<211> LENGTH: 7
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 4

Lys Val Leu Phe Ser Arg Glu
1               5

<210> SEQ ID NO 5
<211> LENGTH: 10
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 5

Arg Leu Gln Ser Gly Asp Ala Leu Arg Val
1               5                   10
```

<210> SEQ ID NO 6
<211> LENGTH: 10
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 6

Arg Ser Pro Gln Leu Gln Asn Leu Arg Asp
 1               5                  10

<210> SEQ ID NO 7
<211> LENGTH: 11
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 7

Arg Ser Arg Asp Pro Ile Tyr Ser Asn Lys Leu
 1               5                  10

<210> SEQ ID NO 8
<211> LENGTH: 12
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 8

Arg Glu Glu Gly Gln Gln Gln Gly Glu Gln Arg Leu
 1               5                  10

<210> SEQ ID NO 9
<211> LENGTH: 13
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 9

Arg Leu Gly Lys Phe Phe Glu Ile Thr Pro Glu Lys Asn
 1               5                  10

<210> SEQ ID NO 10
<211> LENGTH: 13
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 10

Arg Asp Ser Tyr Arg Asn Gln Ala Cys His Ala Arg Cys
 1               5                  10

<210> SEQ ID NO 11
<211> LENGTH: 15
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

```
<400> SEQUENCE: 11

Arg Leu Ile Thr Leu Ala Ile Pro Val Asn Lys Pro Gly Arg Phe
 1               5                  10                  15

<210> SEQ ID NO 12
<211> LENGTH: 14
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 12

Lys Thr Ile Ser Ser Glu Asp Lys Pro Phe Asn Leu Arg Ser
 1               5                  10

<210> SEQ ID NO 13
<211> LENGTH: 15
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 13

Arg Lys Thr Ile Ser Ser Glu Asp Lys Pro Phe Asn Leu Arg Ser
 1               5                  10                  15

<210> SEQ ID NO 14
<211> LENGTH: 15
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 14

Lys Phe Phe Glu Ile Thr Pro Glu Lys Asn Pro Gln Leu Arg Asp
 1               5                  10                  15

<210> SEQ ID NO 15
<211> LENGTH: 17
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 15

Arg Leu Gln Glu Ser Val Ile Val Glu Ile Ser Lys Glu Gln Ile Arg
 1               5                  10                  15

Ala

<210> SEQ ID NO 16
<211> LENGTH: 17
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 16

Lys Val Leu Phe Ser Arg Glu Glu Gly Gln Gln Gly Glu Gln Arg
 1               5                  10                  15

Leu
```

```
<210> SEQ ID NO 17
<211> LENGTH: 18
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 17

Arg Asn Ile Leu Glu Ala Ser Tyr Asp Thr Lys Phe Glu Glu Ile Asn
 1               5                  10                  15

Lys Val

<210> SEQ ID NO 18
<211> LENGTH: 18
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 18

Lys Glu Gln Gln Gln Glu Gln Gln Gln Glu Glu Gln Pro Leu Glu Val
 1               5                  10                  15

Arg Lys

<210> SEQ ID NO 19
<211> LENGTH: 21
<212> TYPE: PRT
<213> ORGANISM: Unknown Organism
<220> FEATURE:
<223> OTHER INFORMATION: Description of Unknown Organism: FLB-1 non-
      transformed or transgenic derived tryptic peptide

<400> SEQUENCE: 19

Arg Val Pro Ser Gly Thr Thr Tyr Tyr Val Val Asn Pro Asp Asn Asn
 1               5                  10                  15

Glu Asn Leu Arg Leu
            20

<210> SEQ ID NO 20
<211> LENGTH: 6
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 20

Lys Glu Gln Ile Arg Gln
 1               5

<210> SEQ ID NO 21
<211> LENGTH: 6
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 21

Arg Gln Ile Glu Arg Gln
 1               5

<210> SEQ ID NO 22
```

```
<211> LENGTH: 6
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 22

Arg Phe Asn Lys Arg Ser
  1               5

<210> SEQ ID NO 23
<211> LENGTH: 7
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 23

Lys Ser Ser Ser Arg Lys Thr
  1               5

<210> SEQ ID NO 24
<211> LENGTH: 7
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 24

Arg Gln Leu Ser Arg Arg Ala
  1               5

<210> SEQ ID NO 25
<211> LENGTH: 10
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 25

Arg Ser Pro Gln Leu Glu Asn Leu Arg Asp
  1               5                  10

<210> SEQ ID NO 26
<211> LENGTH: 12
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 26

Lys Leu Ala Ile Pro Val Asn Lys Pro Gly Arg Tyr
  1               5                  10

<210> SEQ ID NO 27
<211> LENGTH: 11
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 27
```

Lys Arg Ser Pro Gln Leu Glu Asn Leu Arg Asp
  1               5                  10

<210> SEQ ID NO 28
<211> LENGTH: 12
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 28

Arg Val Leu Phe Gly Glu Glu Glu Gln Arg Gln
  1               5                  10

<210> SEQ ID NO 29
<211> LENGTH: 14
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 29

Arg Asn Phe Leu Ala Gly Glu Lys Asp Asn Val Val Arg Gln
  1               5                  10

<210> SEQ ID NO 30
<211> LENGTH: 14
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 30

Lys Thr Ile Ser Ser Glu Asp Glu Pro Phe Asn Leu Arg Ser
  1               5                  10

<210> SEQ ID NO 31
<211> LENGTH: 14
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 31

Lys Gln Lys Gln Glu Glu Glu Pro Leu Glu Val Gln Arg Tyr
  1               5                  10

<210> SEQ ID NO 32
<211> LENGTH: 16
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 32

Arg Lys Thr Ile Ser Ser Glu Asp Glu Pro Phe Asn Leu Arg Ser Ser
  1               5                  10                  15

<210> SEQ ID NO 33
<211> LENGTH: 14
<212> TYPE: PRT
<213> ORGANISM: Unknown Organism
<220> FEATURE:

```
<223> OTHER INFORMATION: Description of Unknown Organism: FLB-4 non-
      transformed or transgenic derived tryptic peptide

<400> SEQUENCE: 33

Lys Val Arg Glu Asp Glu Asn Asn Pro Phe Tyr Phe Arg Ser
  1               5                  10

<210> SEQ ID NO 34
<211> LENGTH: 15
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 34

Lys Phe Phe Glu Ile Thr Pro Glu Lys Asn Pro Gln Leu Arg Asp
  1               5                  10                  15

<210> SEQ ID NO 35
<211> LENGTH: 18
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 35

Arg Gln Val Gln Glu Leu Ala Phe Pro Gly Ser Ala Gln Asp Val Glu
  1               5                  10                  15

Arg Leu

<210> SEQ ID NO 36
<211> LENGTH: 21
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 36

Arg Ile Pro Ala Gly Thr Thr Tyr Tyr Leu Val Asn Pro His Asp His
  1               5                  10                  15

Gln Asn Leu Lys Ile
            20

<210> SEQ ID NO 37
<211> LENGTH: 25
<212> TYPE: PRT
<213> ORGANISM: Unknown Organism
<220> FEATURE:
<223> OTHER INFORMATION: Description of Unknown Organism: FLB-4 non-
      transformed or transgenic derived tryptic peptide

<400> SEQUENCE: 37

Arg Ala Ile Leu Thr Leu Val Asn Asn Asp Asp Arg Asp Ser Tyr Asn
  1               5                  10                  15

Leu His Pro Gly Asp Ala Gln Arg Ile
            20                  25
```